(12) United States Patent
Dyke et al.

(10) Patent No.: US 8,258,152 B2
(45) Date of Patent: Sep. 4, 2012

(54) N-SUBSTITUTED AZAINDOLES AND METHODS OF USE

(75) Inventors: Hazel Joan Dyke, Harlow (GB); Stephen Price, Harlow (GB); Karen Williams, Harlow (GB)

(73) Assignee: Genentech, Inc., South San Francisco, CA (US)

( * ) Notice: Subject to any disclaimer, the term of this patent is extended or adjusted under 35 U.S.C. 154(b) by 162 days.

(21) Appl. No.: 12/664,303

(22) PCT Filed: Jun. 11, 2008

(86) PCT No.: PCT/US2008/066570
§ 371 (c)(1),
(2), (4) Date: May 3, 2010

(87) PCT Pub. No.: WO2008/157179
PCT Pub. Date: Dec. 24, 2008

(65) Prior Publication Data
US 2010/0216768 A1    Aug. 26, 2010

Related U.S. Application Data

(60) Provisional application No. 60/943,441, filed on Jun. 12, 2007.

(51) Int. Cl.
*A01N 43/42* (2006.01)
*A61K 31/44* (2006.01)
*C07D 413/00* (2006.01)

(52) U.S. Cl. ........................................ 514/300; 546/113

(58) Field of Classification Search ........................ None
See application file for complete search history.

(56) References Cited

FOREIGN PATENT DOCUMENTS

| WO | WO 01/64639 | 9/2001 |
|----|----|----|
| WO | WO 02/06213 | 1/2002 |
| WO | WO 03/077855 | 9/2003 |
| WO | WO 03/077914 | 9/2003 |

OTHER PUBLICATIONS

*International Search Report and Written Opinion for International Patent Application No. PCT/US2008/066570.*
Hoshino et al., "Constitutive activation of the 41-/43-kDa mitogen-activated protein kinase signaling pathway in human tumors" *Oncogene* 18:813-822 (1999).
Lewis et al., "Signal transduction through MAP kinase cascades" *Adv Cancer Res.* 74:49-139 (1998).
Price, B., "Putative allosteric MEK1 and MEK2 inhibitors" *Expert Opin. Ther. Patents* 18(6):603-627 (2008).
Sebolt-Leopold et al., "Blockade of the MAP kinase pathway supresses growth of colon tumors in vivo" *Nature Medicine* 5(7):810-816 (Jul. 1999).

*Primary Examiner* — Jeffrey Murry
(74) *Attorney, Agent, or Firm* — Brian L. Buckwalter

(57) ABSTRACT

The invention relates to N-substituted azaindolyl compounds of Formula I with anti-cancer and/or anti-inflammatory activity and more specifically to N-substituted azaindolyl compounds which inhibit MEK kinase activity. The invention provides compositions and methods useful for inhibiting abnormal cell growth or treating a hyperproliferative disorder, or treating an inflammatory disease in a mammal. The invention also relates to methods of using the compounds for in vitro, in situ, and in vivo diagnosis or treatment of mammalian cells, or associated pathological conditions.

11 Claims, No Drawings

N-SUBSTITUTED AZAINDOLES AND METHODS OF USE

RELATED APPLICATION

This application claims the benefit of U.S. Provisional Patent Application No. 60/943,441, filed 12 Jun. 2007, which is incorporated herein by reference in its entirety.

FIELD OF THE INVENTION

The invention relates to N-substituted azaindolyl compounds with anti-cancer activity and more specifically to N-substituted azaindolyl compounds which inhibit MEK kinase activity. The invention also relates to methods of using the compounds for in vitro, in situ, and in vivo diagnosis or treatment of mammalian cells, or associated pathological conditions.

BACKGROUND OF THE INVENTION

In the quest to understand how Ras transmits extracellular growth signals, the MAP (mitogen-activated protein) kinase (MAPK) pathway has emerged as the crucial route between membrane-bound Ras and the nucleus. The MAPK pathway encompasses a cascade of phosphorylation events involving three key kinases, namely Raf, MEK (MAP kinase) and ERK (MAP kinase). Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn et al., *Methods in Enzymology* 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., *Methods in Enzymology* 2001, 332, 417-431). Phosphorylated ERK dimerizes and then translocates to the nucleus where it accumulates (Khokhlatchev et al., *Cell* 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell* 2000, 6, 1343-1354). Overall, treatment of cells with growth factors leads to the activation of ERK1 and 2 which results in proliferation and, in some cases, differentiation (Lewis et al., *Adv. Cancer Res.* 1998, 74, 49-139).

There has been strong evidence that genetic mutations and/or overexpression of protein kinases involved in the MAP kinase pathway lead to uncontrolled cell proliferation and, eventually, tumor formation, in proliferative diseases. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., *Science* 1993, 260, 1834-1837). Recently, bRaf mutations have been identified in more than 60% of malignant melanoma (Davies, H. et al., *Nature* 2002, 417, 949-954). These mutations in bRaf result in a constitutively active MAP kinase cascade. Studies of primary tumor samples and cell lines have also shown constitutive or over-activation of the MAP kinase pathway in cancers of pancreas, colon, lung, ovary and kidney (Hoshino, R. et al., *Oncogene* 1999, 18, 813-822).

MEK has emerged as an attractive therapeutic target in the MAP kinase cascade pathway. MEK, downstream of Ras and Raf, is highly specific for the phosphorylation of MAP kinase; in fact, the only known substrates for MEK phosphorylation are the MAP kinases, ERK1 and 2 Inhibition of MEK has been shown to have potential therapeutic benefit in several studies. For example, small molecule MEK inhibitors have been shown to inhibit human tumor growth in nude mouse xenografts, (Sebolt-Leopold et al., *Nature-Medicine* 1999, 5 (7), 810-816); Trachet et al., AACR Apr. 6-10, 2002, Poster #5426; Tecle, H. IBC 2.sup.nd International Conference of Protein Kinases, Sep. 9-10, 2002), block static allodynia in animals (WO 01/05390 published Jan. 25, 2001) and inhibit growth of acute myeloid leukemia cells (Milella et al., *J Clin Invest* 2001, 108 (6), 851-859).

Several small molecule MEK inhibitors have also been discussed in, for example, WO02/06213, WO 03/077855 and WO03/077914. There still exists a need for new MEK inhibitors as effective and safe therapeutics for treating a variety of proliferative disease states, such as conditions related to the hyperactivity of MEK, as well as diseases modulated by the MEK cascade.

SUMMARY OF THE INVENTION

The invention relates generally to N-substituted azaindolyl compounds of Formula I (and/or solvates, hydrates and/or salts thereof) with anti-cancer and/or anti-inflammatory activity, and more specifically with MEK kinase inhibitory activity. Certain hyperproliferative and inflammatory disorders are characterized by the modulation of MEK kinase function, for example by mutations or overexpression of the proteins. Accordingly, the compounds of the invention and compositions thereof are useful in the treatment of hyperproliferative disorders such as cancer and/or inflammatory diseases such as rheumatoid arthritis.

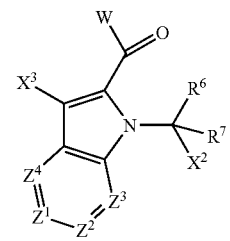

I wherein:
$Z^1$ is $CR^1$ or N;
$Z^2$ is $CR^2$ or N;
$Z^3$ is $CR^3$ or N;
$Z^4$ is $CR^4$ or N;
where one or two of $Z^1$, $Z^2$, $Z^3$, and $Z^4$ are N;
$R^1$, $R^2$, $R^3$ and $R^4$ are independently selected from H, halo, CN, $CF_3$, $-OCF_3$, $-NO_2$, $-(CR^{14}R^{15})_nC(=Y)OR^{11}$, $-(CR^{14}R^{15})_nC(=Y)OR^{11}$, $-(CR^{14}R^{15})_nC(=Y)NR^{11}R^{12}$, $-(CR^{14}R^{15})_nNR^{11}R^{12}$, $-(CR^{14}R^{15})_nOR^{11}$, $-(CR^{14}R^{15})_nSR^{11}$, $-(CR^{14}R^{15})_nNR^{12}C(=Y)R^{11}$, $-(CR^{14}R^{15})_nNR^{12}C(=Y)OR^{11}$, $-(CR^{14}R^{15})_nNR^{13}C(=Y)NR^{11}R^{12}$, $-(CR^{14}R^{15})_nNR^{12}SO_2R^{11}$, $-(CR^{14}R^{15})_nOC(=Y)R^{11}$, $-(CR^{14}R^{15})_nOC(=Y)OR^{11}$, $-(CR^{14}R^{15})_nOC(=Y)NR^{11}R^{12}$, $-(CR^{14}R^{15})_nOS(O)_2(OR^{11})$, $-(CR^{14}R^{15})_nOP(=Y)(OR^{11})(OR^{12})$, $-(CR^{14}R^{15})_nOP(OR^{11})(OR^{12})$, $-(CR^{14}R^{15})_nS(O)R^{11}$, $-(CR^{14}R^{15})_nS(O)_2R^{11}$, $-(CR^{14}R^{15})_nS(O)_2NR^{11}R^{12}$, —(CR$^{14}$R$^{15}$)$_n$S(O)(OR$^{11}$), —(CR$^{14}$R$^{15}$)$_n$S(O)$_2$(OR$^{11}$), —(CR$^{14}$R$^{15}$)$_n$ SC(=Y)R$^{11}$, —(CR$^{14}$R$^{15}$)$_n$SC(=Y)OR$^{11}$, —(CR$^{14}$R$^{15}$)$_n$SC(=Y)NR$^{11}$R$^{12}$, C$_1$-C$_{12}$ alkyl, C$_2$-C$_8$ alkenyl, C$_2$-C$_8$ alkynyl, carbocyclyl, heterocyclyl, aryl, and heteroaryl;

W is

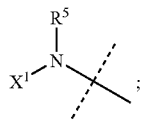

R$^5$, R$^6$ and R$^7$ are independently selected from H or C$_1$-C$_6$ alkyl;

or R$^6$ and R$^7$ together with the carbon atom to which they are attached form a 3-6 membered saturated ring having 0-1 heteroatoms selected from O, S and N, wherein said ring is optionally substituted with one or more groups selected from halo, CN, CF$_3$, —OCF$_3$, C$_1$-C$_6$ alkyl, —OH, —O(C$_1$-C$_6$ alkyl);

X$^1$ is selected from —OR$^{11}$, —NR$^{11}$R$^{12}$, and —S(O)$_2$R$^{11}$; when X$^1$ is —OR$^{11}$, said —OR$^{11}$ and R$^5$ optionally taken together with the nitrogen atom to which they are attached form a 4-7 membered saturated or unsaturated ring having 0-2 additional heteroatoms selected from O, S and N, wherein said ring is optionally substituted with one or more groups selected from halo, CN, CF$_3$, —OCF$_3$, —NO$_2$, oxo, —Si(C$_1$-C$_6$ alkyl), —(CR$^{19}$R$^{20}$)$_n$C(=Y')R$^{16}$, —(CR$^{19}$R$^{20}$)$_n$ C(=Y') OR$^{16}$, —(CR$^{19}$R$^{20}$)$_n$C(=Y')NR$^{16}$R$^{17}$, —(CR$^{19}$R$^{20}$)$_n$ NR$^{16}$R$^{17}$, —(CR$^{19}$R$^{20}$)$_n$OR$^{16}$, —(CR$^{19}$R$^{20}$)$_n$—SR$^{16}$, —(CR$^{19}$R$^{20}$)$_n$ NR$^{16}$C(=Y')R$^{17}$, —(CR$^{19}$R$^{20}$)$_n$ NR$^{16}$C(=Y')OR$^{17}$, —(CR$^{19}$R$^{20}$)$_n$ NR$^{18}$C(=Y')NR$^{16}$R$^{17}$, —(CR$^{19}$R$^{20}$)$_n$NR$^{17}$SO$_2$R$^{16}$, —(CR$^{19}$R$^{20}$)$_n$OC(=Y')R$^{16}$, —(CR$^{19}$R$^{20}$)$_n$OC(=Y')OR$^{16}$, —(CR$^{19}$R$^{20}$)$_n$OC(=Y') NR$^{16}$R$^{17}$, —(CR$^{19}$R$^{20}$)$_n$OS(O)$_2$(OR$^{16}$), —(CR$^{19}$R$^{20}$)$_n$OP(=Y')(OR$^{16}$)(OR$^{17}$), —(CR$^{19}$R$^{20}$)$_n$OP(OR$^{16}$)(OR$^{17}$), —(CR$^{19}$R$^{20}$)$_n$S(O)R$^{16}$, —(CR$^{19}$R$^{20}$)$_n$S(O)$_2$R$^{16}$, —(CR$^{19}$R$^{20}$)$_n$S(O)$_2$NR$^{16}$R$^{17}$, —(CR$^{19}$R$^{20}$)$_n$S(O)(OR$^{16}$), —(CR$^{19}$R$^{20}$)$_n$S(O)$_2$(OR$^{16}$), —(CR$^{19}$R$^{20}$)$_n$ SC(=Y')R$^{16}$, —(CR$^{19}$R$^{20}$)$_n$ SC(=Y')OR$^{16}$, —(CR$^{19}$R$^{20}$)$_n$ SC(=Y') NR$^{16}$R$^{17}$, and R$^{21}$;

X$^2$ is aryl or heteroaryl;

X$^3$ is selected from H, C$_1$-C$_6$ alkyl, halo, CN, CF$_3$, —O(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), and —SO$_2$N(C$_1$-C$_6$ alkyl)$_2$;

R$^{11}$, R$^{12}$ and R$^{13}$ are independently H, C$_1$-C$_{12}$ alkyl, C$_2$-C$_8$ alkenyl, C$_2$-C$_8$ alkynyl, carbocyclyl, heterocyclyl, aryl, or heteroaryl, or R$^{11}$ and R$^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, CF$_3$, —OCF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

R$^{14}$ and R$^{15}$ are independently selected from H, C$_1$-C$_{12}$ alkyl, aryl, carbocyclyl, heterocyclyl, and heteroaryl;

each n is independently selected from 0, 1, 2, 3, 4, 5, or 6;

Y is independently O, NR$^{11}$, or S;

wherein each said alkyl, alkenyl, alkynyl, carbocyclyl, heterocyclyl, aryl and heteroaryl of R$^1$, R$^2$, R$^3$, R$^4$, R$^5$, R$^6$, X$^1$, X$^2$, R$^{11}$, R$^{12}$, R$^{13}$, R$^{14}$, and R$^{15}$ is independently optionally substituted with one or more groups independently selected from halo, CN, CF$_3$, —OCF$_3$, —NO$_2$, oxo, —Si(C$_1$-C$_6$ alkyl), —(CR$^{19}$R$^{20}$)$_n$C(=Y')R$^{16}$, —(CR$^{19}$R$^{20}$)$_n$ C(=Y') OR$^{16}$, —(CR$^{19}$R$^{20}$)$_n$C(=Y')NR$^{16}$R$^{17}$, —(CR$^{19}$R$^{20}$)$_n$ NR$^{16}$R$^{17}$, —(CR$^{19}$R$^{20}$)$_n$OR$^{16}$, —(CR$^{19}$R$^{20}$)$_n$SR$^{16}$, —(CR$^{19}$R$^{20}$)$_n$NR$^{16}$C(=Y')R$^{17}$, —(CR$^{19}$R$^{20}$)$_n$NR$^{16}$C(=Y')OR$^{17}$, —(CR$^{19}$R$^{20}$)$_n$NR$^{18}$C(=Y')NR$^{16}$R$^{17}$, —(CR$^{19}$R$^{20}$)$_n$NR$^{17}$SO$_2$R$^{16}$, —(CR$^{19}$R$^{20}$)$_n$OC(=Y')R$^{16}$, —(CR$^{19}$R$^{20}$)$_n$OC(=Y')OR$^{16}$, —(CR$^{19}$R$^{20}$)$_n$OC(=Y') NR$^{16}$R$^{17}$, —(CR$^{19}$R$^{20}$)$_{10}$S(O)$_2$(OR$^{16}$), —(CR$^{19}$R$^{20}$)$_n$OP(=Y')(OR$^{16}$)(OR$^{17}$), —(CR$^{19}$R$^{20}$)$_n$OP(OR$^{16}$)(OR$^{17}$), —(CR$^{19}$R$^{20}$)$_n$S(O)R$^{16}$, —(CR$^{19}$R$^{20}$)$_n$S(O)$_2$R$^{16}$, —(CR$^{19}$R$^{20}$)$_n$S(O)$_2$NR$^{16}$R$^{17}$, —(CR$^{19}$R$^{20}$)$_n$S(O)(OR$^{16}$), —(CR$^{19}$R$^{20}$)$_n$S(O)$_2$(OR$^{16}$), —(CR$^{19}$R$^{20}$)$_n$SC(=Y')R$^{16}$, —(CR$^{19}$R$^{20}$)$_n$SC(=Y')OR$^{16}$, —(CR$^{19}$R$^{20}$)$_n$SC(=Y') NR$^{16}$R$^{17}$, and R$^{21}$;

each R$^{16}$, R$^{17}$ and R$^{18}$ is independently H, C$_1$-C$_{12}$ alkyl, C$_2$-C$_8$ alkenyl, C$_2$-C$_8$ alkynyl, carbocyclyl, heterocyclyl, aryl, or heteroaryl, wherein said alkyl, alkenyl, alkynyl, carbocyclyl, aryl, or heteroaryl is optionally substituted with one or more groups selected from halo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

or R$^{16}$ and R$^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);

$R^{19}$ and $R^{20}$ are independently selected from H, $C_1$-$C_{12}$ alkyl, —(CH$_2$)$_n$-aryl, —(CH$_2$)$_n$-carbocyclyl, —(CH$_2$)$_n$-heterocyclyl, and —(CH$_2$)$_n$-heteroaryl;

$R^{21}$ is $C_1$-$C_{12}$ alkyl, $C_2$-$C_8$ alkenyl, $C_2$-$C_8$ alkynyl, carbocyclyl, heterocyclyl, aryl, or heteroaryl, wherein each member of $R^{21}$ is optionally substituted with one or more groups selected from halo, oxo, CN, —OCF$_3$, CF$_3$, —NO$_2$, $C_1$-$C_6$ alkyl, —OH, —SH, —O($C_1$-$C_6$ alkyl), —S($C_1$-$C_6$ alkyl), —NH$_2$, —NH($C_1$-$C_6$ alkyl), —N($C_1$-$C_6$ alkyl)$_2$, —SO$_2$ ($C_1$-$C_6$ alkyl), —CO$_2$H, —CO$_2$($C_1$-$C_6$ alkyl), —C(O)NH$_2$, —C(O)NH($C_1$-$C_6$ alkyl), —C(O)N($C_1$-$C_6$ alkyl)$_2$, —N($C_1$-$C_6$ alkyl)C(O)($C_1$-$C_6$ alkyl), —NHC(O)($C_1$-$C_6$ alkyl), —NHSO$_2$($C_1$-$C_6$ alkyl), —N($C_1$-$C_6$ alkyl)SO$_2$($C_1$-$C_6$ alkyl), —SO$_2$NH$_2$, —SO$_2$NH($C_1$-$C_6$ alkyl), —SO$_2$N($C_1$-$C_6$ alkyl)$_2$, —OC(O)NH$_2$, —OC(O)NH($C_1$-$C_6$ alkyl), —OC(O)N($C_1$-$C_6$ alkyl)$_2$, —OC(O)O($C_1$-$C_6$ alkyl), —NHC(O)NH ($C_1$-$C_6$ alkyl), —NHC(O)N($C_1$-$C_6$ alkyl)$_2$, —N($C_1$-$C_6$ alkyl)C(O)NH($C_1$-$C_6$ alkyl), —N($C_1$-$C_6$ alkyl)C(O)N($C_1$-$C_6$ alkyl)$_2$, —NHC(O)NH($C_1$-$C_6$ alkyl), —NHC(O)N($C_1$-$C_6$ alkyl)$_2$, —NHC(O)O($C_1$-$C_6$ alkyl), and —N($C_1$-$C_6$ alkyl)C(O)O($C_1$-$C_6$ alkyl);

each Y' is independently O, NR$^{22}$, or S; and $R^{22}$ is H or $C_1$-$C_{12}$ alkyl.

The present invention includes a composition (e.g., a pharmaceutical composition) comprising a compound of Formula I (and/or solvates, hydrates and/or salts thereof) and a carrier (a pharmaceutically acceptable carrier). The present invention also includes a composition (e.g., a pharmaceutical composition) comprising a compound of Formula I (and/or solvates, hydrates and/or salts thereof) and a carrier (a pharmaceutically acceptable carrier), further comprising a second chemotherapeutic and/or a second anti-inflammatory agent. The present compositions are useful for inhibiting abnormal cell growth or treating a hyperproliferative disorder in a mammal (e.g., human). The present compositions are also useful for treating inflammatory diseases in a mammal (e.g., human).

The present invention includes a method of inhibiting abnormal cell growth or treating a hyperproliferative disorder in a mammal (e.g., human) comprising administering to said mammal a therapeutically effective amount of a compound of Formula I (and/or solvates and salts thereof) or a composition thereof, alone or in combination with a second chemotherapeutic agent.

The present invention includes a method of treating an inflammatory disease in a mammal (e.g., human) comprising administering to said mammal a therapeutically effective amount of a compound of Formula I (and/or solvates and salts thereof) or a composition thereof, alone or in combination with a second anti-inflammatory agent.

The present invention includes a method of using the present compounds for in vitro, in situ, and in vivo diagnosis or treatment of mammalian cells, organisms, or associated pathological conditions.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH (CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH (CH$_3$)CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$, 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like.

The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl (—C≡CH), propynyl (propargyl, —CH$_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronaphthalene, 1,2,3,4-tetrahydronaphthyl, and the like.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "halo" refers to F, Cl, Br or I. The heteroatoms present in heteroaryl or heterocyclcyl include the oxidized forms such as $N^+ \rightarrow O^-$, $S(O)$ and $S(O)_2$.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "abnormal cell growth" and "hyperproliferative disorder" are used interchangeably in this application. "Abnormal cell growth", as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhône-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The term "inflammatory diseases" as used in this application includes, but not limited to, rheumatoid arthritis, atherosclerosis, congestive hear failure, inflammatory bowel disease, chronic obstructive pulmonary disease in the lung, fibrotic disease in the liver and kidney, Crohn's disease, and skin diseases such as psoriasis, eczema, and scleroderma.

An "anti-inflammatory agent" is a compound useful in the treatment of inflammation. Examples of anti-inflammatory agents include injectable protein therapeutics such as Enbrel®, Remicade®, Humira® and Kineret®.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as the PI3 kinase inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" and "compounds of Formula I,", unless otherwise indicated, include compounds of Formula I and stereoisomers, geometric isomers, tautomers, solvates, metabolites, salts (e.g., pharmaceutically acceptable salts) and prodrugs thereof.

The present invention provides N-substituted azaindolyl compounds of Formula I as described above useful as kinase inhibitors, particularly useful as MEK kinase inhibitors. The present invention includes compounds of Formulae I-a, I-b, I-c, I-d, I-e, I-f, I-g, I-h, I-i, and I-j, and all other variables are as defined in Formula I.

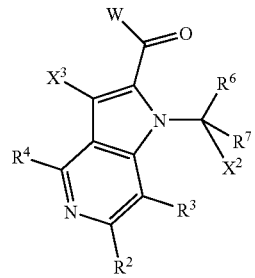

I-a

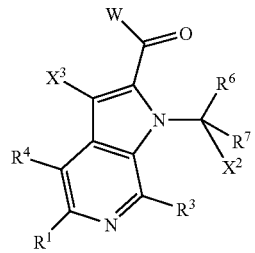

I-b

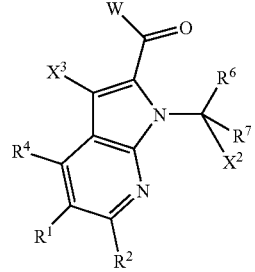

I-c

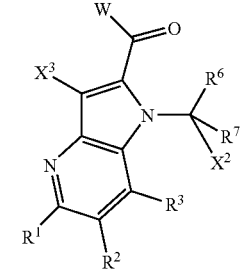

I-d

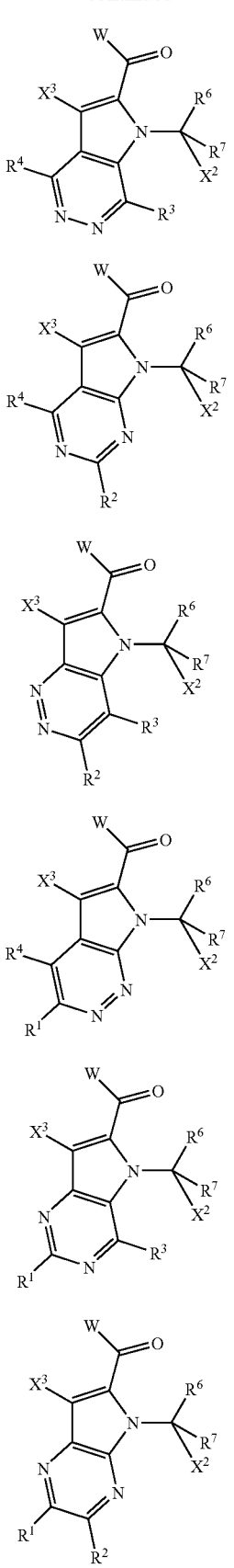

In an embodiment of the present invention, $R^1$ is H, —$OR^{11}$, or $C_1$-$C_6$ alkyl, and all other variables are as defined in Formula I, I-b, I-c, I-d, I-h, I-i, or I-j.

In another embodiment of the present invention, $R^1$ is H, —$OR^{11}$ wherein $R^{11}$ is $C_1$-$C_6$ alkyl, or $C_1$-$C_3$ alkyl; and all other variables are as defined in Formula I, I-b, I-c, I-d, I-h, I-i, or H.

In another embodiment of the present invention, $R^1$ is H, methyl, or —OEt; and all other variables are as defined in Formula I, I-b, I-c, I-d, I-h, I-i, or H.

In an embodiment of the present invention, $R^2$ is H, —$OR^{11}$, or $C_1$-$C_6$ alkyl, and all other variables are as defined in Formula I, I-a, I-c, I-d, I-f, I-g, or I-j, or as defined above.

In another embodiment of the present invention, $R^2$ is H, $C_1$-$C_3$ alkyl, or —$OR^{11}$ wherein $R^{11}$ is $C_1$-$C_6$ alkyl; and all other variables are as defined in Formula I, I-a, I-c, I-d, I-f, I-g, or I-j, or as defined above.

In another embodiment of the present invention, $R^2$ is H, methyl, or —OEt; and all other variables are as defined in Formula I, I-a, I-c, I-d, I-f, I-g, or I-j, or as defined above.

In an embodiment of the present invention, $R^3$ is H, methyl or —Cl; and all other variables are as defined in Formula I, I-a, I-b, I-d, I-e, I-g, or I-i, or as defined above.

In an embodiment of the present invention, $R^4$ is H, halo, $CF_3$, —$OR^{11}$, or $C_1$-$C_6$ alkyl optionally substituted with one or more halo; and all other variables are as defined in Formula I, I-a, I-b, I-c, I-e, I-f, or I-h, or as defined above.

In another embodiment of the present invention, $R^4$ is H, halo, $CF_3$, $C_1$-$C_3$ alkyl optionally substituted with one or more halo, or —$OR^{11}$ wherein $R^{11}$ is $C_1$-$C_6$ alkyl; and all other variables are as defined in Formula I, I-a, I-b, I-c, I-e, I-f, or I-h, or as defined above.

In another embodiment of the present invention, $R^4$ is H, Cl, Br, F, methyl, ethyl, $CHF_2$, $CF_3$, or —OEt; and all other variables are as defined in Formula I, I-a, I-b, I-c, I-e, I-f, or I-h, or as defined above.

In another embodiment of the present invention, $R^4$ is Cl, Br, F, methyl, ethyl, $CHF_2$, or $CF_3$; and all other variables are as defined in Formula I, I-a, I-b, I-c, I-e, I-f, or I-h, or as defined above.

In an embodiment of the present invention, $R^5$ is H or $C_1$-$C_3$ alkyl; and all other variables are as defined in Formula I, or I-a to I-j, or as defined above.

In another embodiment of the present invention, $R^5$ is H or methyl; and all other variables are as defined in Formula I, I-a to I-j, or as defined above.

In another embodiment of the present invention, $R^5$ is H; and all other variables are as defined in Formula I, I-a to I-j, or as defined above.

In another embodiment of the present invention, $R^5$ is methyl; and all other variables are as defined in Formula I, I-a to I-j, or as defined above.

In an embodiment of the present invention, $R^6$ is H or $C_1$-$C_3$ alkyl; and all other variables are as defined in Formula I, I-a to I-j, or as defined above.

In another embodiment of the present invention, $R^6$ is H or methyl; and all other variables are as defined in Formula I, I-a to I-j, or as defined above.

In an embodiment of the present invention, $R^7$ is H or $C_1$-$C_3$ alkyl; and all other variables are as defined in Formula I, I-a to I-j, or as defined above.

In another embodiment of the present invention, $R^7$ is H or methyl; and all other variables are as defined in Formula I, I-a to I-j, or as defined above.

In another embodiment of the present invention, $R^6$ and $R^7$ are taken together with the carbon atom to which they are attached form a cyclopropyl or cyclobutyl ring.

In an embodiment of the present invention, $X^1$ is $OR^{11}$; and all other variables are as defined in Formula I or I-a to I-j; or as defined above.

In an embodiment of the present invention, $X^1$ is $OR^{11}$ wherein $R^{11}$ is H; and all other variables are as defined in Formula I or I-a to I-j; or as defined above.

In another embodiment of the present invention, $X^1$ is $OR^{11}$ wherein $R^{11}$ is $C_1$-$C_{12}$ alkyl (e.g., $C_1$-$C_6$ alkyl) substituted with one or more groups independently selected from halo, CN, $CF_3$, $-OCF_3$, oxo, $-(CR^{19}R^{20})_n$ $C(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_nSR^{16}$, $-(CR^{19}R^{20})_nNR^{16}C(=Y')R^{17}$, $-(CR^{19}R^{20})_n$ $NR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nS(O)R^{16}$, $-(CR^{19}R^{20})_nS(O)_2R^{16}$, $-(CR^{19}R^{20})_n$ $S(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_n$ $SC(=Y')R^{16}$, $-(CR^{19}R^{20})_nSC(=Y')OR^{16}$, $-(CR^{19}R^{20})_nSC(=Y')NR^{16}R^{17}$, and $R^{21}$; and all other variables are as defined in Formula I or I-a to I-j, or as defined above.

In an embodiment of the present invention, $X^1$ is

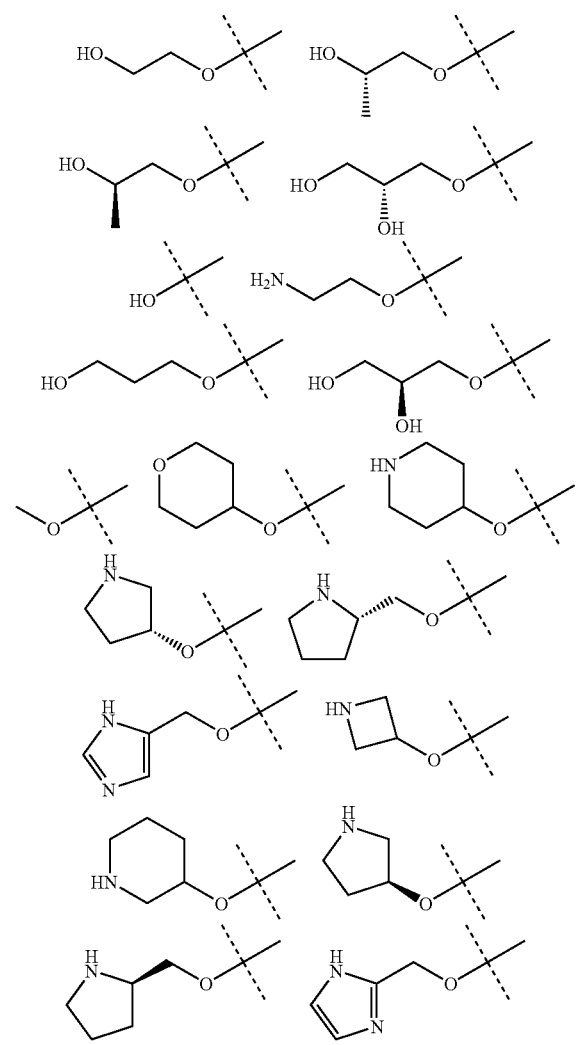

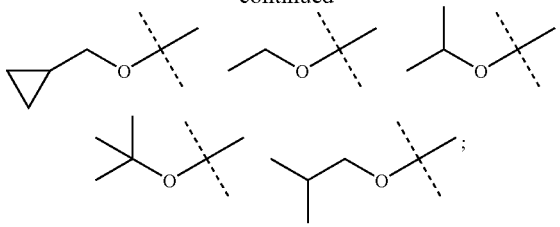

and all other variables are as defined in Formula I or I-a to I-j, or as defined above.

In another embodiment of the present invention, $X^1$ is

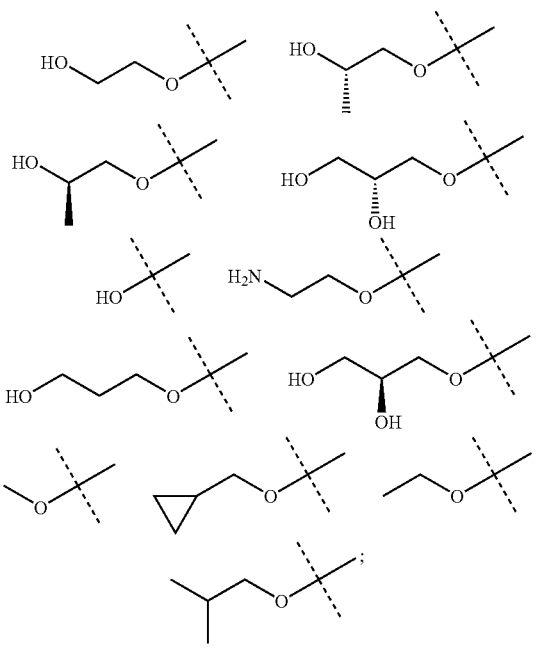

and all other variables are as defined in Formula I or I-a to I-i, or as defined above.

In another embodiment of the present invention, $X^1$ is $OR^{11}$ wherein $R^{11}$ is heterocyclyl (e.g., 4- to 6-membered heterocyclyl) optionally substituted with one or more groups independently selected from halo, CN, $CF_3$, $-OCF_3$, $-NO_2$, oxo, $-(CR^{19}R^{20})_nC(=Y')R^{16}$, $-(CR^{19}R^{20})_nC(=Y')OR^{16}$, $-(CR^{19}R^{20})_nC(=Y'NR^{16}R^{17}$, $-(CR^{19}R^{20})_nNR^{16}R^{17}$, $-(CR^{19}R^{20})_nOR^{16}$, $-(CR^{19}R^{20})_nSR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_n$ $S(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_n$ $SC(=Y')NR^{16}R^{17}$, and $R^{21}$; and all other variables are as defined in Formula I or I-a to I-j, or as defined above.

In another embodiment of the present invention, $X^1$ is $OR^{11}$ wherein $R^{11}$ is 4- to 6-membered heterocyclyl having 1 nitrogen ring atom wherein said heterocyclyl is optionally substituted with one or more groups independently selected from halo, CN, $CF_3$, $-OCF_3$, $-NO_2$, oxo, $-(CR^{19}R^{20})_nC$ $(=Y')R^{16}$, $-(CR^{19}R^{20})_n$ $C(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_nSR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_n$ $NR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_n$ $S(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_n$ $SC(=Y')NR^{16}R^{17}$, and $R^{21}$; and all other variables are as defined in Formula I or I-a to I-j, or as defined above.

In another embodiment of the present invention, $X^1$ is

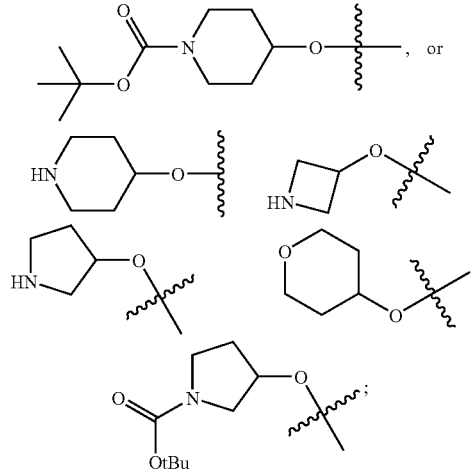

and all other variables are as defined in Formula I or I-a to I-j, or as defined above.

In another embodiment of the present invention, $X^1$ is

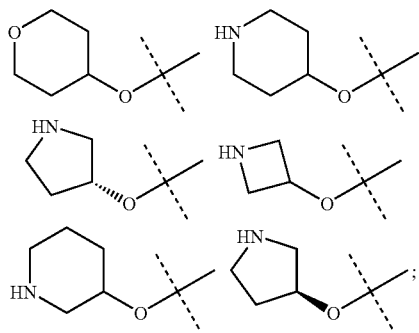

and all other variables are as defined in Formula I or I-a to I-j, or as defined above.

In an embodiment of the present invention, $X^1$ is $-OR^{11}$ and said $-OR^{11}$ and $R^5$ are taken together with the nitrogen atom to which they are attached to form a 5-7 membered saturated or unsaturated cyclic ring having 0-2 additional heteroatoms selected from O, S and N, wherein said cyclic ring is optionally substituted with one or more groups selected from halo, CN, $CF_3$, $-OCF_3$, $-NO_2$, oxo, $-(CR^{19}R^{20})_nC(=Y')R^{16}$, $-(CR^{19}R^{20})_n$ $C(=Y')OR^{16}$, $-(CR^{19}R^{20})_nC(Y')NR^{16}R^{17}$, $-(CR^{19}R^{20})_nNR^{16}R^{17}$, $-(CR^{19}R^{20})_nOR^{16}$, $-(CR^{19}R^{20})_n-SR^{16}$, $-(CR^{19}R^{20})_n$ $NR^{16}C(=Y')R^{17}$, $-(CR^{19}R^{20})_n$ $NR^{16}C(=Y')OR^{17}$, $-(CR^{19}R^{20})_n$ $NR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOS(O)_2(OR^{16})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_n$ $S(O)_2(OR^{16})$, $-(CR^{19}R^{20})_n$ $SC(=Y')R^{16}$, $-(CR^{19}R^{20})_nSC(=Y')OR^{16}$, $-(CR^{19}R^{20})_n$ $SC(=Y')NR^{16}R^{17}$, and $R^{21}$; and all other variables are as defined in Formula I or I-a to I-j, or as defined above.

In another embodiment of the present invention, $X^1$ is $-OR^{11}$ and said $-OR^{11}$ and $R^5$ are taken together with the nitrogen atom to which they are attached to form a 5-6 membered saturated cyclic ring having 0-2 additional heteroatoms selected from O, S and N, wherein said cyclic ring is optionally substituted with one or more groups selected from halo, CN, $CF_3$, $-OCF_3$, $-NO_2$, oxo, $-(CR^{19}R^{20})_nC(=Y')R^{16}$, $-(CR^{19}R^{20})_n$ $C(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_n-SR^{16}$, $-(CR^{19}R^{20})_n$ $NR^{16}C(=Y')R^{17}$, $-(CR^{19}R^{20})_n$ $NR^{16}C(=Y')OR^{17}$, $-(CR^{19}R^{20})_n$ $NR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_n$ $S(O)_2(OR^{16})$, $-(CR^{19}R^{20})_n$ $SC(=Y')R^{16}$, $-(CR^{19}R^{20})_nSC(=Y')OR^{16}$, $-(CR^{19}R^{20})_n$ $SC(=Y')$ $NR^{16}R^{17}$, and $R^{21}$; and all other variables are as defined in Formula I or I-a to I-j, or as defined above.

In another embodiment of the present invention, W is:

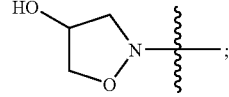

and all other variables are as defined in Formula I or I-a to I-j, or as defined above.

In another embodiment of the present invention, $X^1$ is $-S(O)_2R^{11}$, and all other variables are as defined in Formula I, I-a, I-b, I-c, I-d, I-e, I-f, I-g, I-h, I-i, or I-j, or as defined above.

In another embodiment of the present invention, $X^1$ is $-S(O)_2R^{11}$ wherein $R^{11}$ is H or methyl; and all other variables are as defined in Formula II, I-a, I-b, I-c, I-d, I-e, I-f, I-g, I-h, I-i, or I-j, or as defined above.

In an embodiment of the present invention, $X^2$ is aryl (e.g., phenyl), wherein said aryl is optionally substituted with one or more groups independently selected from halo, CN, $CF_3$, $-OCF_3$, $-NO_2$, oxo, $-Si(C_1-C_6$ alkyl), $-(CR^{19}R^{20})_nC(=Y')R^{16}$, $-(CR^{19}R^{20})_n$ $C(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_n-SR^{16}$, $-(CR^{19}R^{20})_n$ $NR^{16}C(=Y')R^{17}$, $-(CR^{19}R^{20})_n$ $NR^{16}C(=Y')OR^{17}$, $-(CR^{19}R^{20})_n$ $NR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_n$ $OC(=Y')OR^{16}$, $-(CR^{19}R^{20})_n$ $OC(=Y')NR^{16}R^{17}$, $-(CR^{19}R^{20})_n$ $OS(O)_2(OR^{16})$, $-(CR^{19}R^{20})_nS(O)R^{16}$, $-(CR^{19}R^{20})_n$ $S(O)_2R^{16}$, $-(CR^{19}R^{20})_n$ $S(O)_2NR^{16}R^{17}$, $-(CR^{19}R^{20})_n$ $S(O)(OR^{16})$, $-(CR^{19}R^{20})_n$ $S(O)_2(OR^{16})$, $-(CR^{19}R^{20})_n$ $SC(=Y')R^{16}$, $-(CR^{19}R^{20})_nSC(=Y')OR^{16}$, $-(CR^{19}R^{20})_n$ $SC(=Y')NR^{16}R^{17}$, and $R^{21}$; and all other variables are as defined in Formula I, I-a to I-i, II-a to II-i, or III-a to III-i, or as defined above.

In another embodiment of the present invention, $X^2$ is

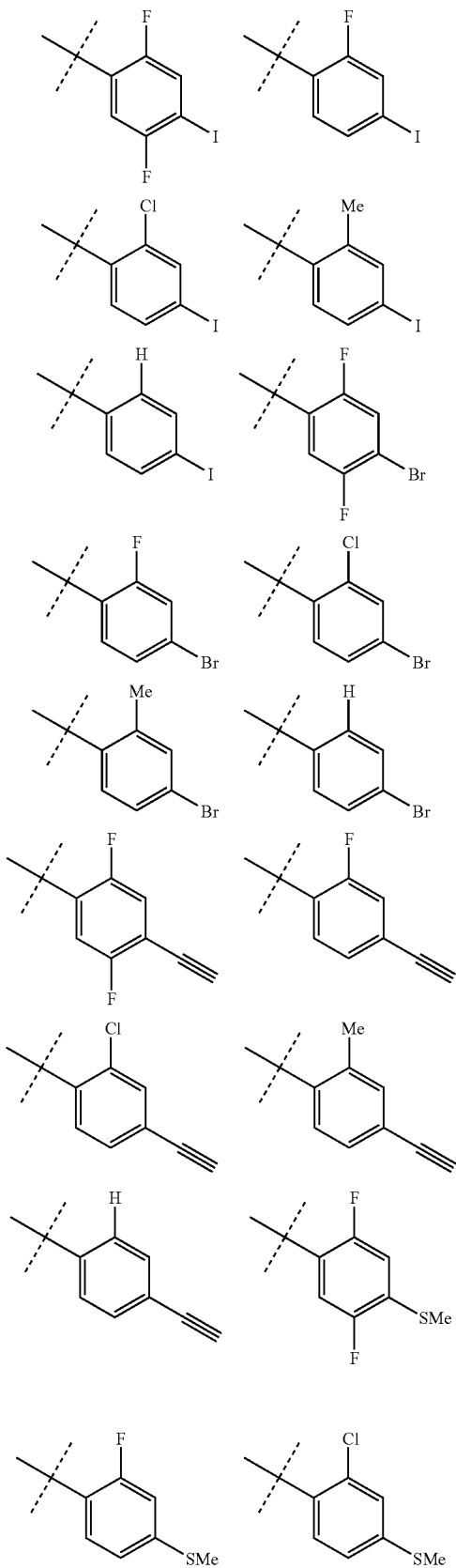

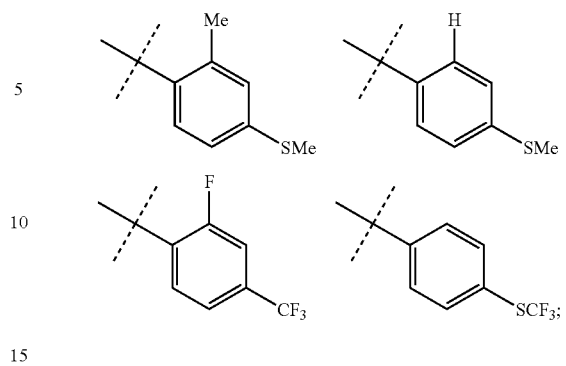

and all other variables are as defined in Formula I, I-a to I-j, or as defined above.

In another embodiment of the present invention, $X^2$ is

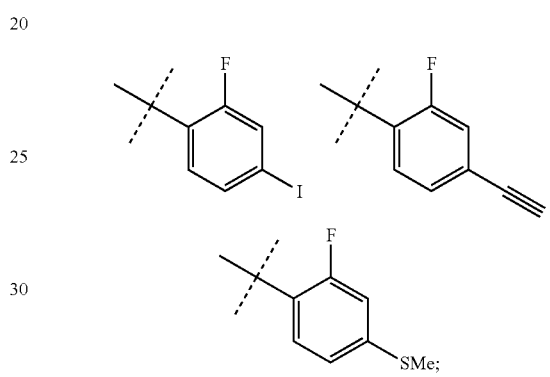

and all other variables are as defined in Formula I, I-a to I-j, or as defined above.

In an embodiment of the present invention, $X^3$ is H, methyl or —Cl; and all other variables are as defined in Formula I, I-a to I-j, or as defined above.

Another embodiment of the present invention includes compounds described in EXAMPLES 5-9 and compounds below:

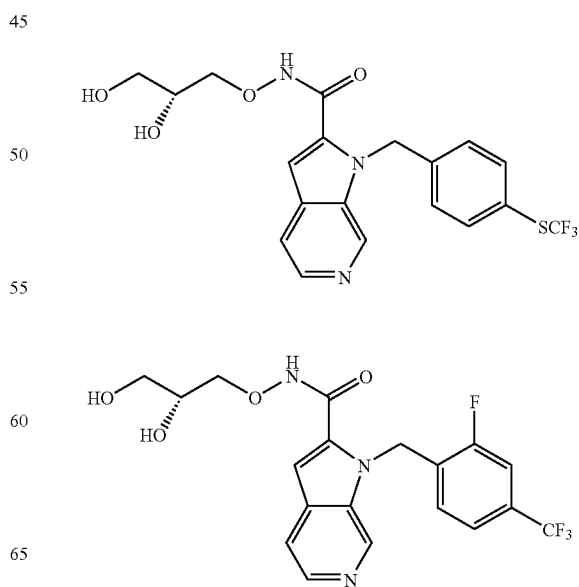

-continued
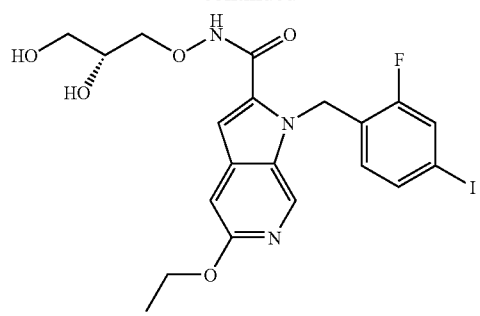
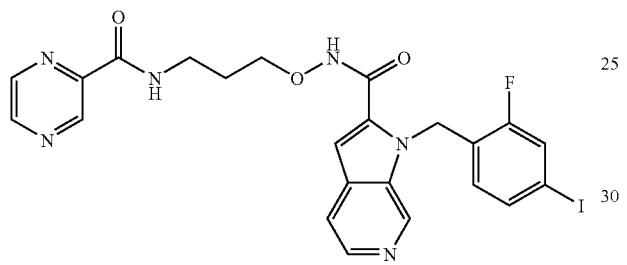
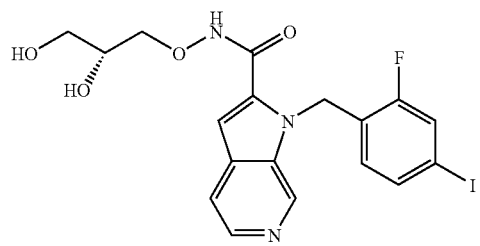
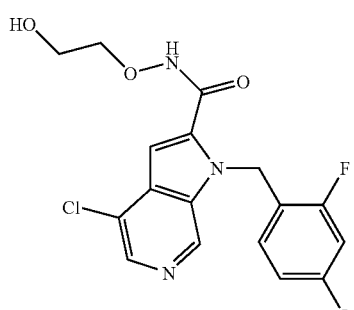
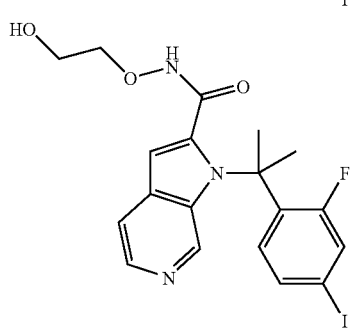
-continued
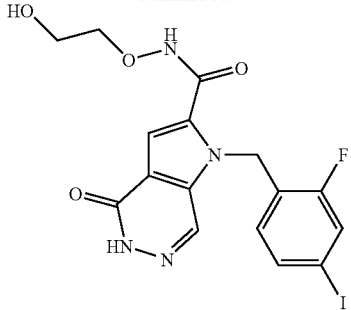
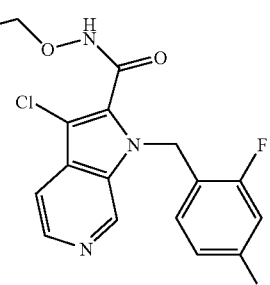
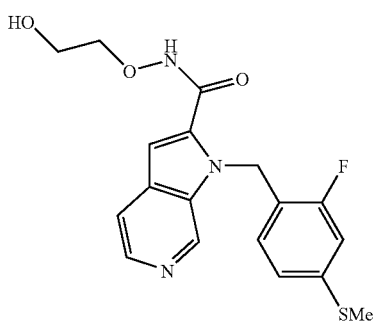
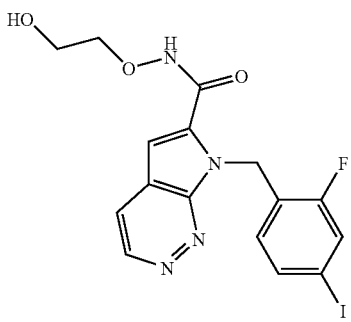
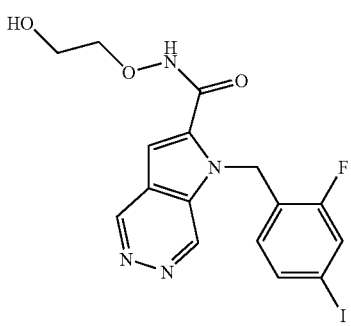

-continued

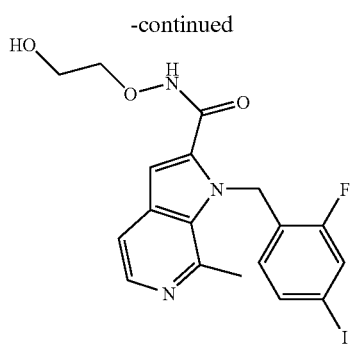

Preparation of Compounds of Formula I

The N-substituted azaindolyl compounds of Formula I are prepared according to the procedures described below in Reaction Scheme 1 and examples or by methods known in the art. The starting materials and various intermediates may be obtained from commercial sources, prepared from commercially available compounds, or prepared using well known synthetic methods.

For example, 6-aza-N-substituted indoles of Formula I-b may be prepared using the synthetic routes outlined in Scheme 1.

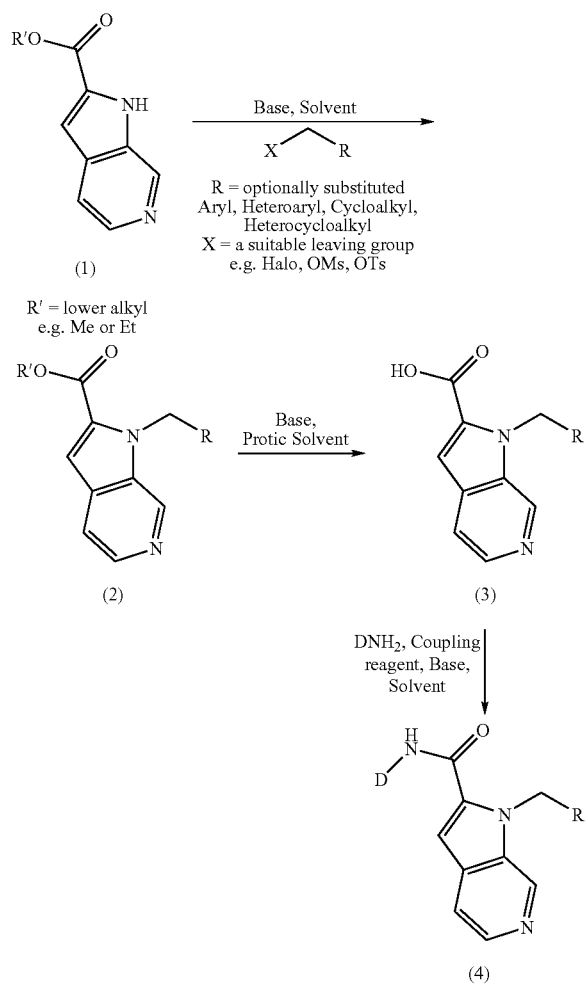

Compounds of formula (1) may be prepared using published methods described in the literature. It will be appreciated that where appropriate functional groups exist, compounds of formula (2) and (3) may be further derivatized by one or more standard synthetic methods employing substitution, oxidation, reduction, or cleavage reactions.

The compounds of the present invention are tested for their capacity to inhibit MEK activity and activation (primary assays) and for their biological effects on growing cells (secondary assays) as described below. The compounds having $IC_{50}$ of less than 5 μM (preferably less than 1 μM, more preferably less than 0.5 μM) in the MEK activity assay of Example 1, $IC_{50}$ of less than 5 μM (preferably less than 0.1 μM, more preferably less than 0.01 μM) in the MEK activation assay of Example 2, $EC_{50}$ of less than 10 μM (preferably less than 5 μM, more preferably less than 0.5 μM) in the cell proliferation assay of Example 3, and/or $EC_{50}$ of less than 10 μM (preferably less than 1 μM, more preferably less than 0.1 μM) in the ERK phosphorylation assay of Example 4, are useful as MEK inhibitors.

The present invention includes a composition (e.g., a pharmaceutical composition) comprising a compound of Formula I (and/or solvates and/or salts thereof) and a carrier (a pharmaceutically acceptable carrier). The present invention also includes a composition (e.g., a pharmaceutical composition) comprising a compound of Formula I (and/or solvates and/or salts thereof) and a carrier (a pharmaceutically acceptable carrier), further comprising a second chemotherapeutic agent such as those described herein. The present compositions are useful for inhibiting abnormal cell growth or treating a hyperproliferative disorder in a mammal (e.g., human). The present compositions are also useful for treating inflammatory diseases in a mammal (e.g., human).

The present invention includes a method of inhibiting abnormal cell growth or treating a hyperproliferative disorder in a mammal (e.g., human) comprising administering to said mammal a therapeutically effective amount of a compound of Formula I (and/or solvates and/or salts thereof) or a composition thereof. Also included in the present invention is a method of treating an inflammatory disease in a mammal (e.g., human) comprising administering to said mammal a therapeutically effective amount of a compound of Formula I (and/or solvates and/or salts thereof) or a composition thereof.

The present invention includes a method of inhibiting abnormal cell growth or treating a hyperproliferative disorder in a mammal (e.g., human) comprising administering to said mammal a therapeutically effective amount of a compound of Formula I (and/or solvates and/or salts thereof) or a composition thereof, in combination with a second chemotherapeutic agent such as those described herein. The present invention also includes a method of treating an inflammatory disease in a mammal (e.g., human) comprising administering to said mammal a therapeutically effective amount of a compound of Formula I (and/or solvates and/or salts thereof) or a composition thereof, in combination with a second anti-inflammatory agent such as those described herein.

The present invention includes a method of using the present compounds for in vitro, in situ, and in vivo diagnosis or treatment of mammalian cells, organisms, or associated pathological conditions.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic or anti-inflammatory agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

EXAMPLES

Abbreviations

DCM Dichloromethane
DIPEA Diisopropylethylamine
DMF Dimethylformamide
EDCI 1-Ethyl-3-(3'-dimethylaminopropyl)carbodiimide
HATU O-(7-Azabenzotriazol-1-yl)-N,N,N',N'-tetramethyluronium hexafluorophosphate
HCl Hydrochloric acid
HOBt 1-Hydroxybenzotriazole
MeOH Methanol
NaHCO$_3$ Sodium bicarbonate
NaOH Sodium hydroxide
Si-SPE Pre-packed Isolute® silica flash chromatography cartridge
THF Tetrahydrofuran General Experimental Conditions $^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography—Mass Spectrometry (LCMS) experiments to determine retention times ($R_T$) and associated mass ions were performed using one of the following methods.

Method A: Experiments performed on a Waters Micromass ZQ quadrupole mass spectrometer linked to a Hewlett Packard HP 1100 LC system with diode array detector. Uses a Higgins Clipeus 5 micron C18 100×3.0 mm column and a 1 ml/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method B: Experiments performed on a Waters Platform LC quadrupole mass spectrometer linked to a Hewlett Packard HP 1100 LC system with diode array detector and 100 position autosampler using a Phenomenex Luna C18(2) 30×4.6 mm column and a 2 ml/minute flow rate. The solvent system was 95% solvent A and 5% solvent B for the first 0.50 minutes followed by a gradient up to 5% solvent A and 95% solvent B over the next 4 minutes. The final solvent system was held constant for a further 0.50 minutes.

Method C: Experiments performed on a Shimadzu LCMS-2010A liquid chromatography mass spectrometer linked to a Shimadzu LC-10AD VP LC system with diode array detector. Uses a Kromasil 100 5 micron C18 50×4.6 mm column and a 2.5 ml/minute flow rate. The initial solvent system was 100% water containing 0.05% trifluoroacetic acid (solvent A) and 0% acetonitrile containing 0.05% trifluoroacetic acid (solvent B), followed by a gradient up to 10% solvent A and 90% solvent B over 7 minutes. The final solvent system was held constant for a further 3 minutes.

Microwave experiments were carried out using a Personal Chemistry Emrys Initiator™ or Optimizer™, which uses a single-mode resonator and dynamic field tuning, both of which give reproducibility and control. Temperatures from 40-250° C. can be achieved, and pressures of up to 20 bar can be reached.

Example 1

MEK Assay (MEK Activity Assay)

Constitutively activated human mutant MEK1 expressed in insect cells is used as source of enzymatic activity at a final concentration in the kinase assay of 62.5 nM.

The assay is carried out for 30 minutes in the presence of 50 μM ATP using recombinant GST-ERK1 produced in *E. Coli* as substrate. Phosphorylation of the substrate is detected and quantified using HTRF reagents supplied by Cisbio. These consist of an anti-GST antibody conjugated to allophycocyanin (XL665) and an anti-phospho (Thr202/Tyr204) ERK antibody conjugated to europium-cryptate. The anti-phospho antibody recognises ERK1 dually phosphorylated on Thr202 and Tyr204. When both antibodies are bound to ERK1 (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multiwell fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

Compounds of Examples 6, 7, and 9 exhibited an $IC_{50}$ of less than 5 μM in the assay described in Example 1.

Example 2 bRaf Assay (MEK Activation Assay)

Constitutively activated bRaf mutant expressed in insect cells is used as source of enzymatic activity.

The assay is carried out for 30 minutes in the presence of 200 μM ATP using recombinant GST-MEK1 produced in *E. Coli* as substrate. Phosphorylation of the substrate is detected and quantified using HTRF, and reagents are supplied by Cisbio. These consist of an anti-GST antibody conjugated to allophycocyanin (XL665) and an anti-phospho (Ser217/Ser221) MEK antibody conjugated to europium-cryptate. The anti-phospho antibody recognises MEK dually phosphorylated on Ser217 and Ser221 or singly phosphorylated on Ser217. When both antibodies are bound to MEK (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multi-well fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

Example 3

Cell Proliferation Assay

Compounds are tested in a cell proliferation assay using the following cell lines:
HCT116 human colorectal carcinoma (ATCC)
A375 human malignant melanoma (ATCC)
Both cell lines are maintained in DMEM/F12 (1:1) media (Gibco) supplemented with 10% FCS at 37° C. in a 5% $CO_2$ humidified incubator.

Cells are seeded in 96-well plates at 2,000 cells/well and after 24 hours they are exposed to different concentrations of compounds in 0.83% DMSO. Cells are grown for a further 72 h, and an equal volume of CellTiter-Glo reagent (Promega) is added to each well. This lyses the cells and generates a luminescent signal proportional to the amount of ATP released (and therefore proportional to the number of cells in the well) that can be detected using a multi-well luminometer.

The $EC_{50}$ is defined as the concentration at which a given compound achieves 50% inhibition of control. $IC_{50}$ values are calculated using the XLfit software package (version 2.0.5).

Example 4

Phospho-ERK Cell-Based Assay

Compounds are tested in a cell-based phospho-ERK ELISA using the following cell lines:
HCT116 human colorectal carcinoma (ATCC)
A375 human malignant melanoma (ATCC)
Both cell lines are maintained in DMEM/F12 (1:1) media (Gibco) supplemented with 10% FCS at 37° C. in a 5% $CO_2$ humidified incubator.

Cells are seeded in 96-well plates at 2,000 cells/well and after 24 h they are exposed to different concentrations of compounds in 0.83% DMSO. Cells are grown for a further 24 h or 2 h, fixed with formaldehyde (2% final) and permeabilised with methanol. Following blocking with TBST-3% BSA, fixed cells are incubated with primary antibody (anti-phospho ERK from rabbit) over-night at 4° C. Cells are incubated with Propidium Iodide (DNA fluorescent dye) and detection of cellular P-ERK is performed using an anti-rabbit secondary antibody conjugated to the fluorescent Alexa Fluor 488 dye (Molecular probes). The fluorescence is analysed using the Acumen Explorer (TTP Labtech), a laser-scanning microplate cytometer, and the Alexa Fluor 488 signal is normalised to the PI signal (proportional to cell number).

The $EC_{50}$ is defined as the concentration at which a given compound achieves a signal half way between the baseline and the maximum response. $EC_{50}$ values are calculated using the XLfit software package (version 2.0.5).

Example 5

4-Methyl-pyridin-3-yl)-carbamic acid tert-butyl ester

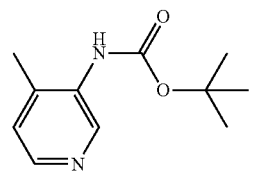

To a solution of di-tert-butyl dicarbonate (11.1 g, 50.9 mmol) in THF (12.5 ml) was added 4-amino-3-picoline (5.0 g, 46.2 mmol) in THF (37.5 ml). The resulting reaction mixture was stirred at room temperature for 3 hours before being concentrated in vacuo to provide a residue. The residue was triturated with heptane whereby the resultant white solid (7.34 g, 74%) was collected by filtration and dried in vacuo. LCMS (Method B): $R_T$=1.61 min, M+H$^+$=209.

1H-Pyrrolo[2,3-c]pyridine-2-carboxylic acid ethyl ester

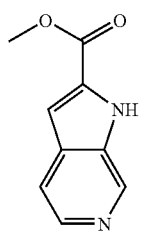

To a solution of (4-methyl-pyridin-3-yl)-carbamic acid tert-butyl ester (3.5 g, 16.8 mmol) in anhydrous THF (30 ml) under an atmosphere of argon at −40° C. was added tert-butyl lithium (20.7 ml, 1.7 M in pentanes, 35.2 mmol). The reaction mixture was maintained at −40° C. for 1 hour before a solution of diethyl oxalate (2.5 ml, 18.5 mmol) in THF (30 ml) was added over a 15 minute period. After stirring for 2 hours at 0° C. the reaction was allowed to warm to room temperature and then stirred for a further 19 hours. 2N HCl (110 ml) was cautiously added to the reaction mixture which was then heated at reflux for 2 hours. After cooling, dichloromethane (100 ml) was added to the reaction mixture and the aqueous phase was adjusted to pH 8 and the organic phase was isolated. The aqueous phase was washed with dichloromethane (2×50 ml) and the combined organic layers were dried over magnesium sulfate, then concentrated to afford a light-brown solid. The material was triturated with ethyl acetate and the resultant solid was then collected by filtration to afford the desired product as a beige solid (586 mg, 18%). LCMS (Method B): $R_T$=1.89 min, M+H$^+$=190.

Ethyl 1-(2-fluoro-4-iodo-benzyl)-1H-pyrrolo[2,3-c]pyridine-2-carboxylate

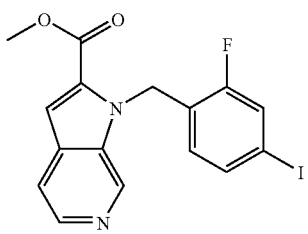

To a suspension of methyl 1H-pyrrolo[2,3-c]pyridine-2-carboxylate (0.81 g, 4.26 mmol) in DMF (15 ml) was added potassium tert-butoxide (0.72 g, 6.39 mmol). After the resultant red-brown suspension had been stirred for 40 minutes, a solution of 2-fluoro-4-iodobenzyl bromide (2.01 g, 6.39 mmol) in DMF (5 ml) was added dropwise over 10 minutes. The suspension was then heated to 60° C. for 35 minutes before stirring at room temperature for 18 hours. The reaction mixture was concentrated in vacuo, the resultant residue partitioned between dichloromethane (40 ml) and water (30 ml) and the organic layer separated. The aqueous layer was extracted with dichloromethane (2×25 ml) and the combined organic extracts were washed with brine (30 ml) dried over magnesium sulphate, then concentrated in vacuo to provide a residue. The residue was purified by flash chromatography (Si-SPE, dichloromethane:ethyl acetate 100:0 to 50:50 to 0:100 then dichloromethane:methanol 90:10 to 80:20) gave the title compound as a pale cream solid (0.83 g, 46%). LCMS (method B): $R_T$=2.58 min, M+H$^+$=425.

Sodium 1-(2-fluoro-4-iodo-benzyl)-1H-pyrrolo[2,3-c]pyridine-2-carboxylate

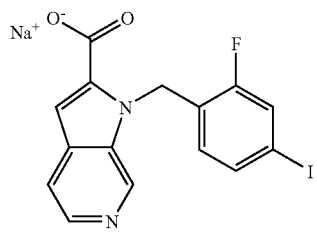

To a solution of methyl 1-(2-fluoro-4-iodo-benzyl)-1H-pyrrolo[2,3-c]pyridine-2-carboxylate (0.46 g, 1.09 mmol) in methanol (4 ml) was added 1M aqueous solution of sodium hydroxide (1.4 ml, 1.40 mmol) and the reaction was heated at reflux for 1.5 hours. The reaction mixture was concentrated in vacuo and azeotroped with toluene (15 ml), methanol (15 ml), toluene (15 ml) and dichloromethane to afford the crude title compound as a waxy white solid (0.50 g, quantitative yield). LCMS (method B): $R_T$=2.11 min, (M−H)$^−$=395; M+H$^+$=397.

1-(2-Fluoro-4-iodo-benzyl)-1H-pyrrolo[2,3-c]pyridine-2-carboxylic acid ((R)-2,2-dimethyl-[1,3]-dioxolan-4-ylmethoxy)-amide

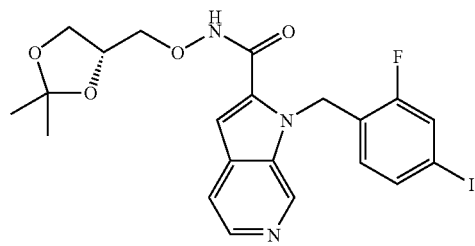

EDCI (259 mg, 1.08 mmol) and HOBt (204 mg, 1.51 mmol) were added to a suspension of sodium 1-(2-fluoro-4-iodo-benzyl)-1H-pyrrolo[2,3-c]pyridine-2-carboxylate (494 mg, 1.08 mmol) in THF (7 ml). The suspension was warmed gently for 1 minute before the addition of a solution of O—((R)-2,2-dimethyl-[1,3]dioxolan-4-ylmethyl)-hydroxylamine (222 mg, 1.51 mmol) in THF (3 ml) followed by DIPEA (0.19 ml, 1.10 mmol). The reaction mixture was stirred at room temperature for 18 hours, poured into ethyl acetate (60 ml) and washed sequentially with 0.1M HCl (10 ml), saturated NaHCO$_3$ solution (10 ml) and brine (10 ml). The organic layer was isolated and dried over magnesium sulphate, then concentrated in vacuo to provide a residue. Trituration of the residue in dichloromethane afforded the title compound as a pale cream solid (0.433 g, 76%). LCMS (method B): $R_T$=2.32 min, (M+H)$^+$=524, M+H$^+$=526.

1-(2-Fluoro-4-iodo-benzyl)-1H-pyrrolo[2,3-c]pyridine-2-carboxylic acid ((R)-2,3-dihydroxy-propoxy)-amide

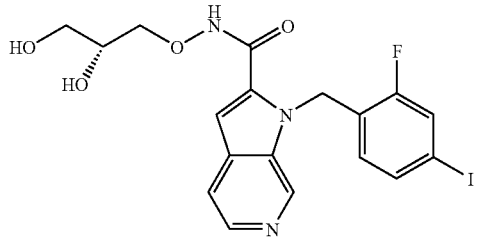

1-(2-Fluoro-4-iodo-benzyl)-1H-pyrrolo[2,3-c]pyridine-2-carboxylic acid ((R)-2,2-dimethyl-[1,3]dioxolan-4-ylmethoxy)-amide (29 mg, 0.06 mmol) was dissolved in 0.067 M methanolic HCl solution (2.3 ml, 0.15 mmol) and stirred at room temperature for 1.5 hours. The reaction mixture was concentrated in vacuo then azeotroped with toluene (2×15 ml). Purification by flash chromatography (NH$_2$-SPE, dichloromethane, ethyl acetate, 20:80 methanol:dichloromethane, 5:35:60 triethylamine:methanol:dichloromethane) followed by trituration in acetonitrile afforded the product as a cream solid (13 mg, 49%). LCMS (Method A): $R_T$=4.53 min, (M−H)$^−$=484, M+H$^+$=486. $^1$H NMR (CD$_3$OD): 3.60 (2H, m), 3.85 (1H, m), 3.91 (1H, dd, J=10.2, 6.8 Hz), 4.02 (1H, dd, J=10.2, 3.8 Hz), 5.93 (2H, s), 6.66 (1H, t, J=8.0 Hz), 7.13 (1H, s), 7.43 (1H, dd, J=8.0, 1.6 Hz), 7.52 (1H, dd, J=9.7, 1.6 Hz), 7.80 (1H, d, J=5.5 Hz), 8.22 (1H, d, br, J=5.5 Hz), 8.97 (1H, s).

Example 6

1-(2-Fluoro-4-iodo-benzyl)-1H-pyrrolo[2,3-c]pyridine-2-carboxylic acid cyclopropylmethoxy-amide

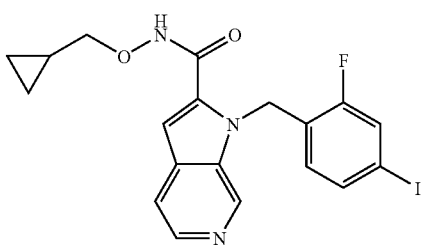

HATU (67 mg, 0.18 mmol) and triethylamine (50 μL, 0.35 mmol) were added to a solution of sodium 1-(2-fluoro-4-iodo-benzyl)-1H-pyrrolo[2,3-c]pyridine-2-carboxylate (49 mg, 0.12 mmol) and O-cyclopropylmethyl-hydroxylamine hydrochloride (21.8 mg, 0.178 mmol) in DMF (500 μL). The reaction mixture was stirred at room temperature for 18 h, then a further 11 mg (0.09 mmol) of O-cyclopropylmethyl-hydroxylamine hydrochloride, 33 mg (0.09 mmol) of HATU, and 50 μL (0.35 mmol) of triethylamine was added. Stirring was continued for a further 18 h, then the reaction mixture was poured into ethyl acetate (15 mL). The organic layer was washed with a 1:1 solution of saturated NaHCO$_3$ and brine (10 mL), dried over Na$_2$SO$_4$, filtered and concentrated to afford a yellow oil. The crude product was purified by reversed phase HPLC to afford the title compound as a white powder (TFA salt, 39 mg, 57%). LCMS (Method C): $R_T$=3.17 min, M+H$^+$=466. $^1$H NMR (DMSO-D$_6$): δ=0.21 (m, 2H), 0.51 (m, 2H), 1.00 (m, 1H), 3.60 (d, J=7.2 Hz, 2H), 5.96 (s, 2H), 6.61 (t, J=8.0 Hz, 1H), 7.33 (s, 1H), 7.47 (dd, J=8.0, 1.2 Hz, 1H), 7.68 (dd, J=9.6, 1.6 Hz, 1H), 8.24 (d, J=6.4 Hz, 1H), 8.43 (d, J=6.4 Hz, 1H), 9.52 (s, 1H).

Example 7

1-(2-Fluoro-4-iodobenzyl)-N-(2-hydroxyethoxy)-1H-pyrrolo[2,3-c]pyridine-2-carboxamide

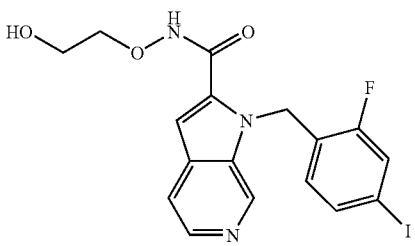

To a solution of ethyl 1-(2-fluoro-4-iodobenzyl)-1H-pyrrolo[2,3-c]pyridine-2-carboxylate (78 mg, 0.183 mmol) in methanol (1.0 ml) was added 1 N NaOH (0.19 ml) and water (0.66 ml). The reaction mixture was stirred at 90° C. for 1 hour. The solvents were evaporated in vacuo, and the residue azeotroped with toluene to afford a while solid. The solid was dissolved in DMF (2.0 ml), and then O-(2-vinyloxy-ethyl)-hydroxylamine (23 mg, 0.220 mmol) and HATU (104 mg, 0.275 mmol) were added. The reaction mixture was stirred at room temperature under nitrogen for 18 hours. Water (20 ml) was added, and the mixture was extracted with ethyl acetate (20 ml) twice. The ethyl acetate solutions were combined and washed with water (10 ml) once, brine (10 ml) once, dried with MgSO$_4$, and concentrated to a crude oil. The crude oil was purified by flash column chromatography to afford 88 mg of an oil. The oil was dissolved in ethanol (2.0 ml) and 1 N aqueous HCl (0.4 ml) was added. The reaction mixture was stirred overnight at room temperature, concentrated to a crude oil, and purified by RPHPLC to afford the title compound as a white powder (TFA salt, 29 mg, 31%). LCMS (Method C): $R_T$=2.17 min, M+H$^+$=456. $^1$H NMR (DMSO-D$_6$): δ=3.56 (t, J=4.8 Hz, 2H), 3.86 (t, J=4.8 Hz, 2H), 5.97 (s, 2H), 6.62 (t, J=8.0 Hz, 1H), 7.36 (s, 1H), 7.48 (dd, J=8.0, 1.2 Hz, 1H), 7.68 (dd, J=10 Hz, 1.6 Hz, 1H), 8.24 (d, J=6 Hz, 1H), 8.44 (d, J=6.4 Hz, 1H), 9.51 (s, 1H), 12.33 (s, 1H).

Example 8

1-(4-Ethynyl-2-fluoro-benzyl)-1H-pyrrolo[2,3-c]pyridine-2-carboxylic acid ((R)-2,2-dimethyl-[1,3]dioxolan-4-ylmethoxy)-amide

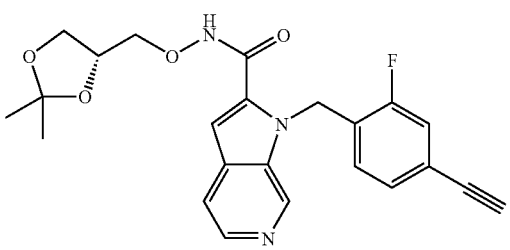

Palladium (II) acetate (1.5 mg, 5 µmol) was added to a mixture of 1-(2-fluoro-4-iodo-benzyl)-1H-pyrrolo[2,3-c]pyridine-2-carboxylic acid ((R)-2,2-dimethyl-[1,3]-dioxolan-4-ylmethoxy)-amide (55 mg, 0.11 mmol), trimethylsilylacetylene (138 µl, 1.0 mmol) and triphenylphosphine (3 mg, 10 µmol) in piperidine (0.5 ml). The resultant mixture was heated at 150° C. under microwave irradiation for 10 seconds. The reaction mixture was diluted with ethyl acetate (35 ml) and washed sequentially with water (10 ml), then brine (10 ml). The organic layer was isolated, dried over magnesium sulphate and concentrated in vacuo to provide a residue. The residue was dissolved in methanol (5 ml) to which potassium carbonate (29 mg, 0.21 mmol) was added, and the resultant suspension was stirred at room temperature for 2 hours. The reaction mixture was filtered, concentrated in vacuo, and then partitioned between ethyl acetate (25 ml) and water (20 ml). The organic layer was isolated, dried over magnesium sulphate and concentrated in vacuo to provide a residue. Purification by flash chromatography (Si-SPE, dichloromethane: ethyl acetate, 100:0 to 70:30 to 40:60 to 0:100) afforded the title compound as a yellow solid (30 mg, 68%). LCMS (method B): $R_T$=2.21 min, $(M-H)^-$=422, $(M+H)^+$=424.

1-(4-Ethynyl-2-fluoro-benzyl)-1H-pyrrolo[2,3-c]pyridine-2-carboxylic acid ((R)-2,3-dihydroxy-propoxy)-amide

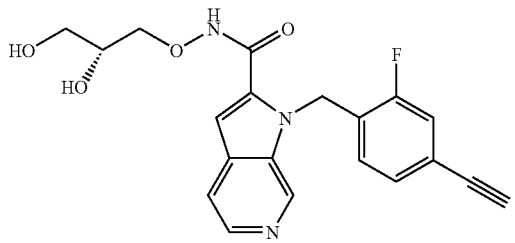

1-(4-Ethynyl-2-fluoro-benzyl)-1H-pyrrolo[2,3-c]pyridine-2-carboxylic acid ((R)-2,2-dimethyl-[1,3]dioxolan-4-ylmethoxy)-amide (30 mg, 0.07 mmol) was dissolved in 0.067 M methanolic HCl solution (3 ml, 0.20 mmol) and stirred at room temperature for 1.5 hours. The reaction mixture was concentrated in vacuo then azeotroped with toluene (2×15 ml) to give a solid residue. Purification of the solid residue by flash chromatography (NH$_2$-SPE, dichloromethane, ethyl acetate, 20:80 methanol:dichloromethane, 5:35:60 triethylamine:methanol: dichloromethane) followed by trituration in acetonitrile afforded the product as a cream solid (5 mg, 18%). LCMS (Method A): $R_T$=4.03 min, $(M-H)^-$=382, $M+H^+$=384. $^1$H NMR (CD$_3$OD): 3.58 (1H, s), 3.60 (2H, m), 3.85 (1H, m), 3.91 (1H, dd, J=10.2, 6.8 Hz), 4.03 (1H, dd, J=10.2, 3.8 Hz), 5.97 (2H, s), 6.84 (1H, t, J=7.9 Hz), 7.11 (1H, s), 7.16 (1H, dd, J=7.9, 1.5 Hz), 7.21 (1H, dd, J=10.8, 1.5 Hz), 7.76 (1H, d, J=5.6 Hz), 8.22 (1H, d, br, J=5.6 Hz), 8.93 (1H, s).

Example 9

Methyl 4-bromo-1-(2-fluoro-4-iodo-benzyl)-1H-pyrrolo[2,3-c]pyridine-2-carboxylate and tert-Butyl 4-bromo-1-(2-fluoro-4-iodo-benzyl)-1H-pyrrolo[2,3-c]pyridine-2-carboxylate

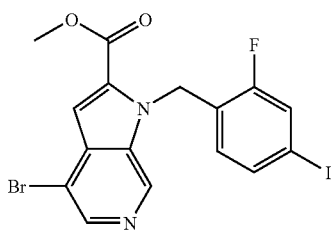

-continued

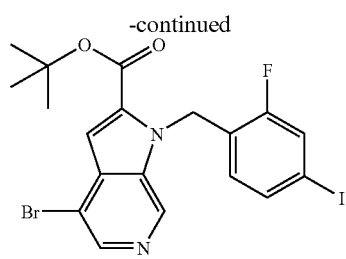

To a suspension of methyl 4-bromo-1H-pyrrolo[2,3-c]pyridine-2-carboxylate[1] (0.59 g, 2.31 mmol) in DMF (10 ml) was added potassium tert-butoxide (0.39 g, 3.47 mmol). After the red-brown suspension had been stirred for 30 minutes, a solution of 2-fluoro-4-iodobenzyl bromide (1.24 g, 3.93 mmol) in DMF (4 ml) was added dropwise over 10 minutes. The suspension was then heated to 60° C. for 45 minutes before stirring at room temperature for 18 hours. The reaction mixture was concentrated in vacuo to give a residue. The residue was partitioned between dichloromethane (30 ml) and water (30 ml) and the organic layer separated. The aqueous layer was extracted with dichloromethane (2×25 ml) and the combined organic extracts were dried over magnesium sulphate and concentrated in vacuo to give a residue. Purification of the resultant residue by flash chromatography (Si-SPE, dichloromethane:ethyl acetate 100:0 to 60:40 to 40:60 to 0:100 then dichloromethane:methanol 90:10 to 80:20) gave a 1:2 mixture of the title compounds (methyl ester/transesterified tert-butyl ester) as a waxy yellow solid (0.21 g, 18%) that was used without further purification.

Sodium 4-bromo-1-(2-fluoro-4-iodo-benzyl)-1H-pyrrolo[2,3-c]pyridine-2-carboxylate

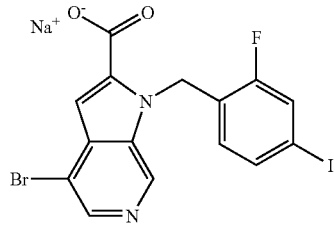

To a solution of methyl/tert-butyl 4-bromo-1-(2-fluoro-4-iodo-benzyl)-1H-pyrrolo[2,3-c]pyridine-2-carboxylate (0.21 g, 0.41 mmol) in methanol (4 ml) was added 1M aqueous solution of sodium hydroxide (0.54 ml, 0.54 mmol), and the reaction was heated at reflux for 1 hour. The reaction mixture was concentrated in vacuo then azeotroped with toluene (15 ml), methanol (15 ml), toluene (15 ml) and dichloromethane to afford the crude title compound as a waxy white solid (0.23 g, quantitative yield). LCMS (method B): $R_T$=3.24 min, $(M-H)^-$=473, 475; $M+H^+$=475, 477.

4-Bromo-1-(2-fluoro-4-iodo-benzyl)-1H-pyrrolo[2,3-c]pyridine-2-carboxylic acid ((R)-2,2-dimethyl-[1,3]-dioxolan-4-ylmethoxy)-amide

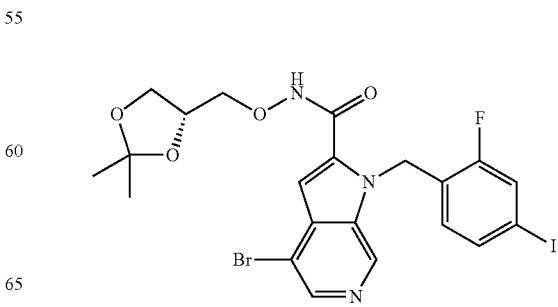

EDCI (99 mg, 0.52 mmol) and HOBt (78 mg, 0.58 mmol) were added to a suspension of sodium 4-bromo-1-(2-fluoro-4-iodo-benzyl)-1H-pyrrolo[2,3-c]pyridine-2-carboxylate (0.23 g, 0.41 mmol) in THF (4 ml). The suspension was warmed gently for 1 minute before the addition of a solution of O—((R)-2,2-dimethyl-[1,3]dioxolan-4-ylmethyl)-hydroxylamine (85 mg, 0.58 mmol) in THF (1 ml), followed by DIPEA (73 µl, 0.42 mmol). The reaction mixture was stirred at room temperature for 70 hours, poured into ethyl acetate (40 ml) then washed sequentially with 0.1M HCl (10 ml), saturated NaHCO$_3$ solution (10 ml) and brine (10 ml). The organic layer was isolated then dried over magnesium sulphate and concentrated in vacuo to provide a solid residue. Purification of the residue by flash chromatography (Si-SPE, dichloromethane:ethyl acetate 100:0 to 70:30 to 40:60 to 0:100) afforded the title compound as a waxy white solid (0.17 g, 68%). LCMS (method B): $R_T$=3.51 min, M+H$^+$=604, 606.

4-Bromo-1-(2-fluoro-4-iodo-benzyl)-1H-pyrrolo[2,3-c]pyridine-2-carboxylic acid ((R)-2,3-dihydroxypropoxy)-amide

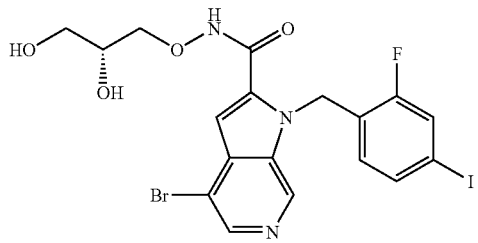

A solution of 4-bromo-1-(2-fluoro-4-iodo-benzyl)-1H-pyrrolo[2,3-c]pyridine-2-carboxylic acid ((R)-2,2-dimethyl-[1,3]dioxolan-4-ylmethoxy)-amide (40 mg, 66 µmol) in dichloromethane (1.5 ml) was loaded onto a SCX-2 SPE cartridge. The desired compound was eluted from the cartridge with a solution of ammonia in methanol to afford a residue. The residue was further purified by flash chromatography (Si-SPE, ethyl acetate, dichloromethane:methanol 90:10 to 80:20) afforded the title compound as a pale yellow gum (5 mg, 13%). LCMS (Method A): $R_T$=3.51 min, (M−H)$^−$=562, 564, M+H$^+$=564, 566. $^1$H NMR (CD$_3$OD): 3.62 (2H, m), 3.89 (1H, m), 3.94 (1H, dd, J=10.2, 6.4 Hz), 4.05 (1H, dd, J=10.2, 3.7 Hz), 5.92 (2H, s), 6.63 (1H, t, J=8.0 Hz), 7.04 (1H, s), 7.40 (1H, dd, J=8.0, 1.6 Hz), 7.49 (1H, dd, J=9.7, 1.6 Hz), 8.29 (1H, s), 8.79 (1H, s).

We claim:
1. A compound selected from Formula I:

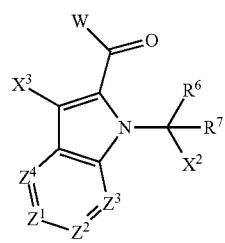

or a salt thereof, wherein:
$Z^1$ is CR$^1$;
$Z^2$ is N;
$Z^3$ is CR$^3$;
$Z^4$ is CR$^4$;
$R^1$, $R^3$ and $R^4$ are independently selected from H or halo;
W is

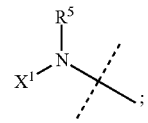

$R^5$, $R^6$ and $R^7$ are independently selected from H or C$_1$-C$_6$ alkyl;
or $R^6$ and $R^7$ together with the carbon atom to which they are attached form a 3-6 membered saturated ring having 0-1 heteroatoms selected from O, S and N, wherein said ring is optionally substituted with one or more groups selected from halo, CN, CF$_3$, —OCF$_3$, C$_1$-C$_6$ alkyl, —OH, —O(C$_1$-C$_6$ alkyl);
$X^1$ is selected from —OR$^{11}$, —NR$^{11}$R$^{12}$, and —S(O)$_2$R$^{11}$; when $X^1$ is —OR$^{11}$, said —OR$^{11}$ and R$^5$ optionally taken together with the nitrogen atom to which they are attached form a 4-7 membered saturated or unsaturated ring having 0-2 additional heteroatoms selected from O, S and N, wherein said ring is optionally substituted with one or more groups selected from halo, CN, CF$_3$, —OCF$_3$, —NO$_2$, oxo, —Si(C$_1$-C$_6$ alkyl), —(CR$^{19}$R$^{20}$)$_n$C(=Y')R$^{16}$, —(CR$^{19}$R$^{20}$)$_n$C(=Y')OR$^{16}$, —(CR$^{19}$R$^{20}$)$_n$C(=Y')NR$^{16}$R$^{17}$, —(CR$^{19}$R$^{20}$)$_n$NR$^{16}$R$^{17}$, —(CR$^{19}$R$^{20}$)$_n$OR$^{16}$, —(CR$^{19}$R$^{20}$)$_n$SR$^{16}$, —(CR$^{19}$R$^{20}$)$_n$NR$^{16}$C(=Y')R$^{17}$, —(CR$^{19}$R$^{20}$)$_n$NR$^{16}$C(=Y')OR$^{17}$, —(CR$^{19}$R$^{20}$)$_n$NR$^{18}$C(=Y')NR$^{16}$R$^{17}$, —(CR$^{19}$R$^{20}$)$_n$NR$^{17}$SO$_2$R$^{16}$, —(CR$^{19}$R$^{20}$)$_n$OC(=Y')R$^{16}$, —(CR$^{19}$R$^{20}$)$_n$OC(=Y')OR$^{16}$, —(CR$^{19}$R$^{20}$)$_n$OC(=Y')NR$^{16}$R$^{17}$, —(CR$^{19}$R$^{20}$)$_n$OS(O)$_2$(OR$^{16}$), —(CR$^{19}$R$^{20}$)$_n$OP(=Y')(OR$^{16}$)(OR$^{17}$), —(CR$^{19}$R$^{20}$)$_n$OP(OR$^{16}$)(OR$^{17}$), —(CR$^{19}$R$^{20}$)$_n$S(O)R$^{16}$, —(CR$^{19}$R$^{20}$)$_n$S(O)$_2$R$^{16}$, —(CR$^{19}$R$^{20}$)$_n$S(O)$_2$NR$^{16}$R$^{17}$, —(CR$^{19}$R$^{20}$)$_n$S(O)(OR$^{16}$), —(CR$^{19}$R$^{20}$)$_n$S(O)$_2$(OR$^{16}$), —(CR$^{19}$R$^{20}$)$_n$SC(=Y')R$^{16}$, —(CR$^{19}$R$^{20}$)$_n$SC(=Y')OR$^{16}$, —(CR$^{19}$R$^{20}$)$_n$SC(=Y')NR$^{16}$R$^{17}$, and R$^{21}$;
$X^2$ is phenyl;
$X^3$ is selected from H;
$R^{11}$, $R^{12}$ and $R^{13}$ are independently H, C$_1$-C$_{12}$ alkyl, C$_2$-C$_8$ alkenyl, C$_2$-C$_8$ alkynyl, carbocyclyl, heterocyclyl, aryl, or heteroaryl,
or $R^{11}$ and $R^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, CF$_3$, —OCF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH (C₁-C₆ alkyl), —NHC(O)N(C₁-C₆ alkyl)₂, —NHC(O)O(C₁-C₆ alkyl), and —N(C₁-C₆ alkyl)C(O)O(C₁-C₆ alkyl);

$R^{14}$ and $R^{15}$ are independently selected from H, $C_1$-$C_{12}$ alkyl, aryl, carbocyclyl, heterocyclyl, and heteroaryl;

each n is independently selected from 0, 1, 2, 3, 4, 5, or 6;

Y is independently O, $NR^{11}$, or S;

wherein each said alkyl, alkenyl, alkynyl, carbocyclyl, heterocyclyl, aryl and heteroaryl of $R^1$, $R^2$, $R^3$, $R^4$, $R^5$, $R^6$, $X^1$, $X^2$, $R^{11}$, $R^{12}$, $R^{13}$, $R^{14}$, and $R^{15}$ is independently optionally substituted with one or more groups independently selected from halo, CN, CF₃, —OCF₃, —NO₂, oxo, —Si(C₁-C₆ alkyl), —(CR¹⁹R²⁰)ₙC(=Y')R¹⁶, —(CR¹⁹R²⁰)ₙC(=Y')OR¹⁶, —(CR¹⁹R²⁰)ₙC(=Y')NR¹⁶R¹⁷, —(CR¹⁹R²⁰)ₙNR¹⁶R¹⁷, —(CR¹⁹R²⁰)ₙOR¹⁶, —(CR¹⁹R²⁰)ₙSR¹⁶, —(CR¹⁹R²⁰)ₙNR¹⁶C(=Y')R¹⁷, —(CR¹⁹R²⁰)ₙNR¹⁶C(=Y')OR¹⁷, —(CR¹⁹R²⁰)ₙNR¹⁸C(=Y')NR¹⁶R¹⁷, —(CR¹⁹R²⁰)ₙNR¹⁷SO₂R¹⁶, —(CR¹⁹R²⁰)ₙOC(=Y')R¹⁶, —(CR¹⁹R²⁰)ₙOC(=Y')(OR¹⁶, —(CR¹⁹R²⁰)ₙOC(=Y')NR¹⁶R¹⁷, —(CR¹⁹R²⁰)ₙOS(O)₂(OR¹⁶), —(CR¹⁹R²⁰)ₙOP(=Y')(OR¹⁶)(OR¹⁷), —(CR¹⁹R²⁰)ₙOP(OR¹⁶)(OR¹⁷), —(CR¹⁹R²⁰)ₙS(O)R¹⁶, —(CR¹⁹R²⁰)ₙS(O)₂R¹⁶, —(CR¹⁹R²⁰)ₙS(O)₂NR¹⁶R¹⁷, —(CR¹⁹R²⁰)ₙS(O)(OR¹⁶), —(CR¹⁹R²⁰)ₙS(O)₂(OR¹⁶), —(CR¹⁹R²⁰)ₙSC(=Y')R¹⁶, —(CR¹⁹R²⁰)ₙSC(=Y')OR¹⁶, —(CR¹⁹R²⁰)ₙSC(=Y)NR¹⁶R¹⁷, and $R^{21}$;

each $R^{16}$, $R^{17}$ and $R^{18}$ is independently H, $C_1$-$C_{12}$ alkyl, $C_2$-$C_8$ alkenyl, $C_2$-$C_8$ alkynyl, carbocyclyl, heterocyclyl, aryl, or heteroaryl, wherein said alkyl, alkenyl, alkynyl, carbocyclyl, heterocyclyl, aryl, or heteroaryl is optionally substituted with one or more groups selected from halo, CN, —OCF₃, CF₃, —NO₂, C₁-C₆ alkyl, —OH, —SH, —O(C₁-C₆ alkyl), —S(C₁-C₆ alkyl), —NH₂, —NH(C₁-C₆ alkyl), —N(C₁-C₆ alkyl)₂, —SO₂(C₁-C₆ alkyl), —CO₂H, —CO₂(C₁-C₆ alkyl), —C(O)NH₂, —C(O)NH(C₁-C₆ alkyl), —C(O)N(C₁-C₆ alkyl)₂, —N(C₁-C₆ alkyl)C(O)(C₁-C₆ alkyl), —NHC(O)(C₁-C₆ alkyl), —NHSO₂(C₁-C₆ alkyl), —N(C₁-C₆ alkyl)SO₂(C₁-C₆ alkyl), —SO₂NH₂, —SO₂NH(C₁-C₆ alkyl), —SO₂N(C₁-C₆ alkyl)₂, —OC(O)NH₂, —OC(O)NH(C₁-C₆ alkyl), —OC(O)N(C₁-C₆ alkyl)₂, —OC(O)O(C₁-C₆ alkyl), —NHC(O)NH(C₁-C₆ alkyl), —NHC(O)N(C₁-C₆ alkyl)₂, —N(C₁-C₆ alkyl)C(O)NH(C₁-C₆ alkyl), —N(C₁-C₆ alkyl)C(O)N(C₁-C₆ alkyl)₂, —NHC(O)NH(C₁-C₆ alkyl), —NHC(O)N(C₁-C₆ alkyl)₂, —NHC(O)O(C₁-C₆ alkyl), and —N(C₁-C₆ alkyl)C(O)O(C₁-C₆ alkyl);

or $R^{16}$ and $R^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, —OCF₃, CF₃, —NO₂, C₁-C₆ alkyl, —OH, —SH, —O(C₁-C₆ alkyl), —S(C₁-C₆ alkyl), —NH₂, —NH(C₁-C₆ alkyl), —N(C₁-C₆ alkyl)₂, —SO₂(C₁-C₆ alkyl), —CO₂H, —CO₂(C₁-C₆ alkyl), —C(O)NH₂, —C(O)NH(C₁-C₆ alkyl), —C(O)N(C₁-C₆ alkyl)₂, C₆ alkyl)C(O)(C₁-C₆ alkyl), —NHC(O)(C₁-C₆ alkyl), —NHSO₂(C₁-C₆ alkyl), —N(C₁-C₆ alkyl)SO₂(C₁-C₆ alkyl), —SO₂NH₂, —SO₂NH(C₁-C₆ alkyl), —SO₂N(C₁-C₆ alkyl)₂, —OC(O)NH₂, —OC(O)NH(C₁-C₆ alkyl), —OC(O)N(C₁-C₆ alkyl)₂, —OC(O)O(C₁-C₆ alkyl), —NHC(O)NH(C₁-C₆ alkyl), —NHC(O)N(C₁-C₆ alkyl)₂, —N(C₁-C₆ alkyl)C(O)NH(C₁-C₆ alkyl), —N(C₁-C₆ alkyl)C(O)N(C₁-C₆ alkyl)₂, —NHC(O)NH(C₁-C₆ alkyl), —NHC(O)N(C₁-C₆ alkyl)₂, —NHC(O)O(C₁-C₆ alkyl), and —N(C₁-C₆ alkyl)C(O)O(C₁-C₆ alkyl);

$R^{19}$ and $R^{20}$ are independently selected from H, $C_1$-$C_{12}$ alkyl, —(CH₂)ₙ-aryl, —(CH₂)ₙ-carbocyclyl, —(CH₂)ₙ-heterocyclyl, and —(CH₂)ₙ-heteroaryl;

$R^{21}$ is $C_1$-$C_{12}$ alkyl, $C_2$-$C_8$ alkenyl, $C_2$-$C_8$ alkynyl, carbocyclyl, heterocyclyl, aryl, or heteroaryl, wherein each member of $R^{21}$ is optionally substituted with one or more groups selected from halo, oxo, CN, —OCF₃, CF₃, —NO₂, C₁-C₆ alkyl, —OH, —SH, —O(C₁-C₆ alkyl), —S(C₁-C₆ alkyl), —NH₂, —NH(C₁-C₆ alkyl), —N(C₁-C₆ alkyl)₂, —SO₂(C₁-C₆ alkyl), —CO₂H, —CO₂(C₁-C₆ alkyl), —C(O)NH₂, —C(O)NH(C₁-C₆ alkyl), —C(O)N(C₁-C₆ alkyl)₂, —N(C₁-C₆ alkyl)C(O)(C₁-C₆ alkyl), —NHC(O)(C₁-C₆ alkyl), —NHSO₂(C₁-C₆ alkyl), —N(C₁-C₆ alkyl)SO₂(C₁-C₆ alkyl), —SO₂NH₂, —SO₂NH(C₁-C₆ alkyl), —SO₂N(C₁-C₆ alkyl)₂, —OC(O)NH₂, —OC(O)NH(C₁-C₆ alkyl), —OC(O)N(C₁-C₆ alkyl)₂, —OC(O)O(C₁-C₆ alkyl), —NHC(O)NH(C₁-C₆ alkyl), —NHC(O)N(C₁-C₆ alkyl)₂, —N(C₁-C₆ alkyl)C(O)NH(C₁-C₆ alkyl), —N(C₁-C₆ alkyl)C(O)N(C₁-C₆ alkyl)₂, —NHC(O)NH(C₁-C₆ alkyl), —NHC(O)N(C₁-C₆ alkyl)₂, —NHC(O)O(C₁-C₆ alkyl), and —N(C₁-C₆ alkyl)C(O)O(C₁-C₆ alkyl);

each Y' is independently O, $NR^{22}$, or S; and $R^{22}$ is H or $C_1$-$C_{12}$ alkyl.

2. The compound of claim 1 wherein $X^1$ is selected from:

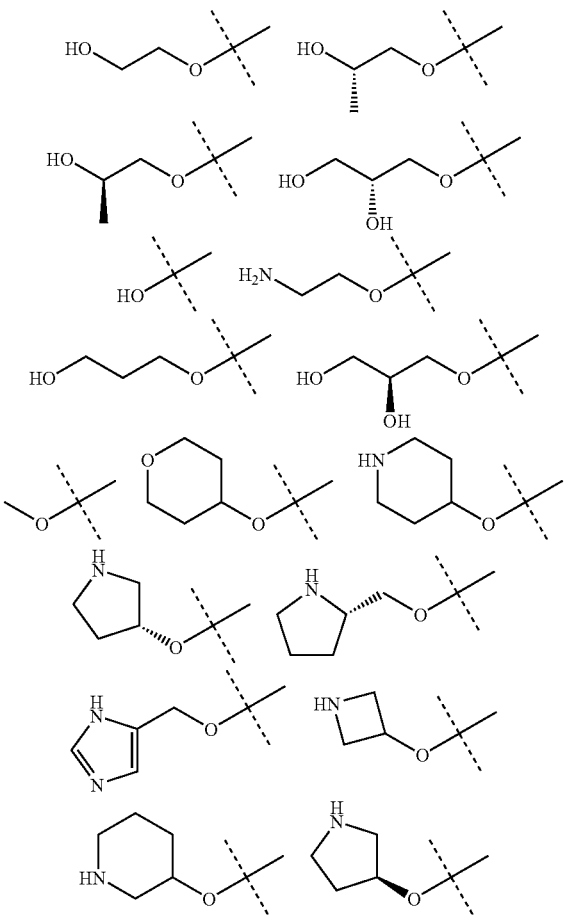

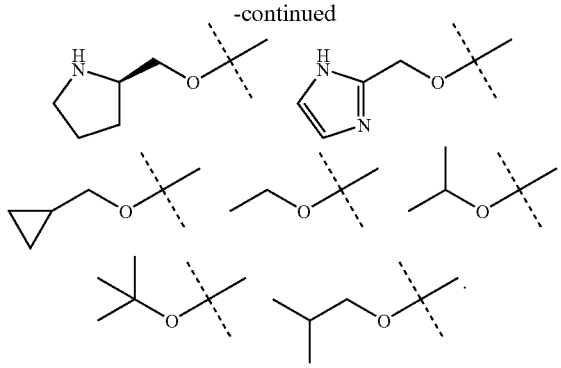

3. The compound of claim 2 wherein $X^1$ is selected from:

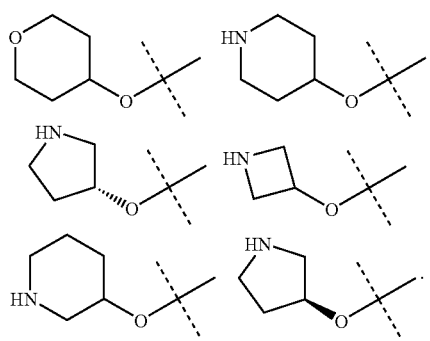

4. The compound of claim 1 wherein $X^2$ is selected from:

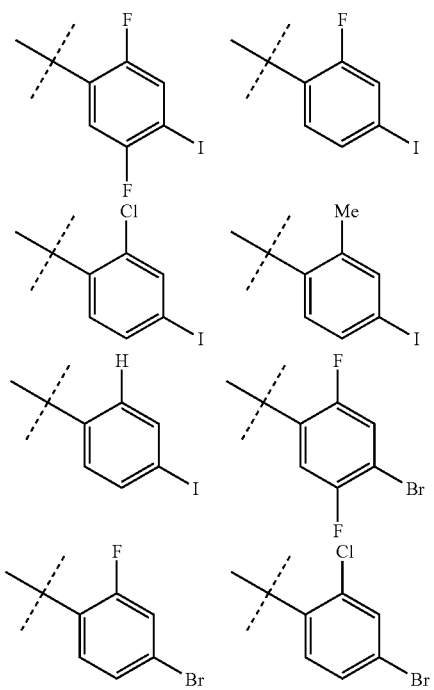

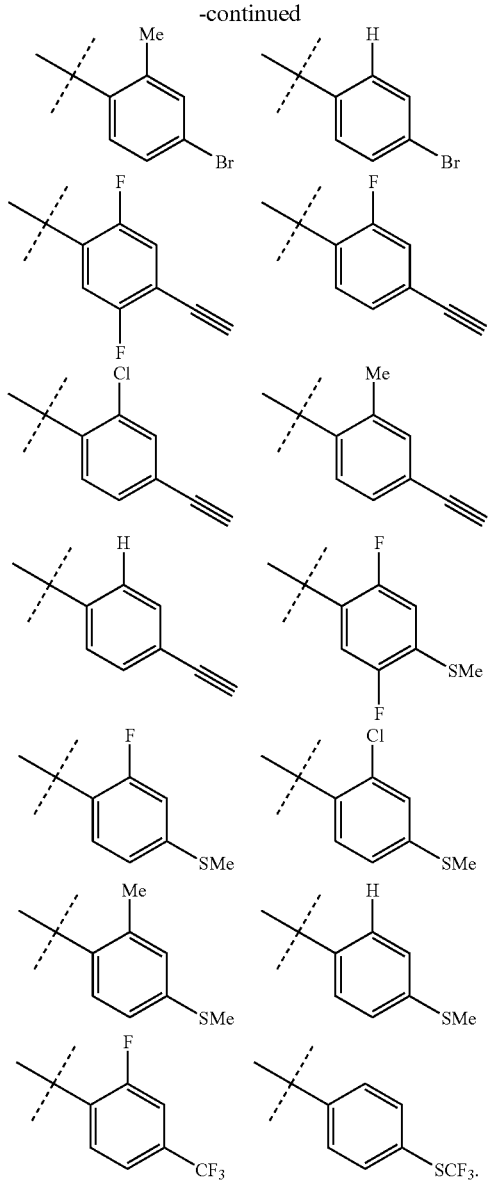

5. The compound of claim 1 wherein $R^3$ is selected from H.

6. The compound of claim 1 wherein $R^4$ is selected from Cl, Br, F.

7. The compound of claim 1 wherein $R^5$ is H.

8. The compound of claim 1 wherein $R^6$ is H or methyl.

9. The compound of claim 1 wherein $R^7$ is H or methyl.

10. The compound of claim 1 wherein $R^6$ and $R^7$ are taken together with the carbon atom to which they are attached to form a cyclopropyl or cyclobutyl ring.

11. A pharmaceutical composition comprising a compound of claim 1, and a pharmaceutically acceptable carrier.

* * * * *

UNITED STATES PATENT AND TRADEMARK OFFICE
CERTIFICATE OF CORRECTION

PATENT NO. : 8,258,152 B2 Page 1 of 1
APPLICATION NO. : 12/664303
DATED : September 4, 2012
INVENTOR(S) : Dyke et al.

It is certified that error appears in the above-identified patent and that said Letters Patent is hereby corrected as shown below:

Under Column 39, line 60, before $C_6$, second occurrence, please insert --$N(C_1$- --.

Signed and Sealed this
Twenty-third Day of October, 2012

David J. Kappos
*Director of the United States Patent and Trademark Office*